(12) United States Patent
Høgset

(10) Patent No.: US 12,263,182 B2
(45) Date of Patent: Apr. 1, 2025

(54) METHOD OF INTRODUCING AN mRNA MOLECULE INTO A CELL

(71) Applicant: PCI Biotech AS, Oslo (NO)

(72) Inventor: Anders Høgset, Oslo (NO)

(73) Assignee: PCI BIOTECH AS, Oslo (NO)

(*) Notice: Subject to any disclaimer, the term of this patent is extended or adjusted under 35 U.S.C. 154(b) by 1211 days.

(21) Appl. No.: 16/963,583

(22) PCT Filed: Jan. 24, 2019

(86) PCT No.: PCT/EP2019/051749
§ 371 (c)(1),
(2) Date: Jul. 21, 2020

(87) PCT Pub. No.: WO2019/145419
PCT Pub. Date: Aug. 1, 2019

(65) Prior Publication Data
US 2021/0052628 A1 Feb. 25, 2021

(30) Foreign Application Priority Data
Jan. 24, 2018 (GB) ...................................... 1801169

(51) Int. Cl.
A61K 31/7105 (2006.01)
A61K 41/00 (2020.01)
C07C 13/00 (2006.01)

(52) U.S. Cl.
CPC ...... *A61K 31/7105* (2013.01); *A61K 41/0071* (2013.01); *C07C 13/00* (2013.01)

(58) Field of Classification Search
CPC ........................ A61K 31/7105; A61K 41/0071
See application file for complete search history.

(56) References Cited

U.S. PATENT DOCUMENTS

| | | | |
|---|---|---|---|
| 6,680,301 B2 | 1/2004 | Berg et al. | |
| 2002/0155099 A1* | 10/2002 | Berg | A61P 35/00 435/6.12 |
| 2004/0096425 A1 | 5/2004 | Hogset et al. | |
| 2015/0202293 A1* | 7/2015 | Berg | A61K 47/61 435/375 |
| 2018/0228763 A1 | 8/2018 | Cheng et al. | |

FOREIGN PATENT DOCUMENTS

| | | |
|---|---|---|
| CN | 1484706 | 3/2004 |
| CN | 101550428 | 10/2009 |
| CN | 105833275 | 8/2016 |
| WO | 96/07432 | 3/1996 |
| WO | 00/54802 | 9/2000 |
| WO | 02/44395 | 6/2002 |
| WO | 02/44396 | 6/2002 |
| WO | 03/020309 | 3/2003 |
| WO | 2008/007073 | 1/2008 |
| WO | 2013/189663 | 12/2013 |
| WO | 2014/139597 | 9/2014 |

OTHER PUBLICATIONS

International Search Report and Written Opinion of the International Searching Authority, issued Apr. 5, 2019 in corresponding International Patent Application No. PCT/EP2019/051749.
Bøe et al., "Light-induced Gene Expression Using Messenger RNA Molecules", Oligonucleotides, 20(1): 1-6 (2010).
Berg, K. et al., "Photochemical Internalization: A Novel Technology for Delivery of Macromolecules into Cytosol", Cancer Research, vol. 59, (Mar. 15, 1999), pp. 1180-1183.
Berg, K. et al., "Site-Specific Drug Delivery by Photochemical Internalization Enhances the Antitumor Effect of Bleomycin", Clin Cancer Res., vol. 11, No. 23 (Dec. 1, 2005), pp. 8476-8485.
Bettinger, T. et al., "Peptide-mediated RNA delivery: a novel approach for enhanced transfection of primary and post-mitotic cells", Nucleic Acids Research (2001), vol. 29, No. 18, pp. 3882-3891.
Bøe, S.L. et al., "Light-Induced mRNA Transfection", in Synthetic Messenger RNA and Cell Metabolism Modulation Methods and Protocols, Methods Mol. Biol. (2013), vol. 969, pp. 89-100, Humana Press, P. M. Rabinovich ed.
Bøe, S.L. et al., "Enhancing nucleic acid delivery by photochemical internalization", Ther. Deliv. (2013), vol. 4, No. 9, pp. 1125-1140.
Bøe, S. et al., "Photochemically Induced Gene Silencing Using Small Interfering RNA Molecules in Combination with Lipid Carriers", Oligonucleotides (2007), vol. 17, pp. 166-173.

(Continued)

*Primary Examiner* — Ekaterina Poliakova-Georgantas
(74) *Attorney, Agent, or Firm* — Wenderoth, Lind & Ponack, L.L.P.

(57) ABSTRACT

The present invention concerns an in vivo method for introducing an mRNA molecule (which is not associated with a carrier) into the cytosol of a cell(s) in a subject, by the use of photochemical internalization, wherein the photosensitising agent is a sulphonated meso-tetraphenyl chlorin, sulfonated tetraphenylporphine or a di- or tetrasulfonated aluminium phthalocyanine used in an amount of 0.0001 to 1 μg. The method may be used to express a polypeptide in the subject. The invention is also directed to pharmaceutical compositions containing the photosensitising agents and the mRNA and uses of the molecules in therapy, e.g. to treat or prevent cancer or an infection.

29 Claims, 7 Drawing Sheets

(56) References Cited

OTHER PUBLICATIONS

Figure 1:
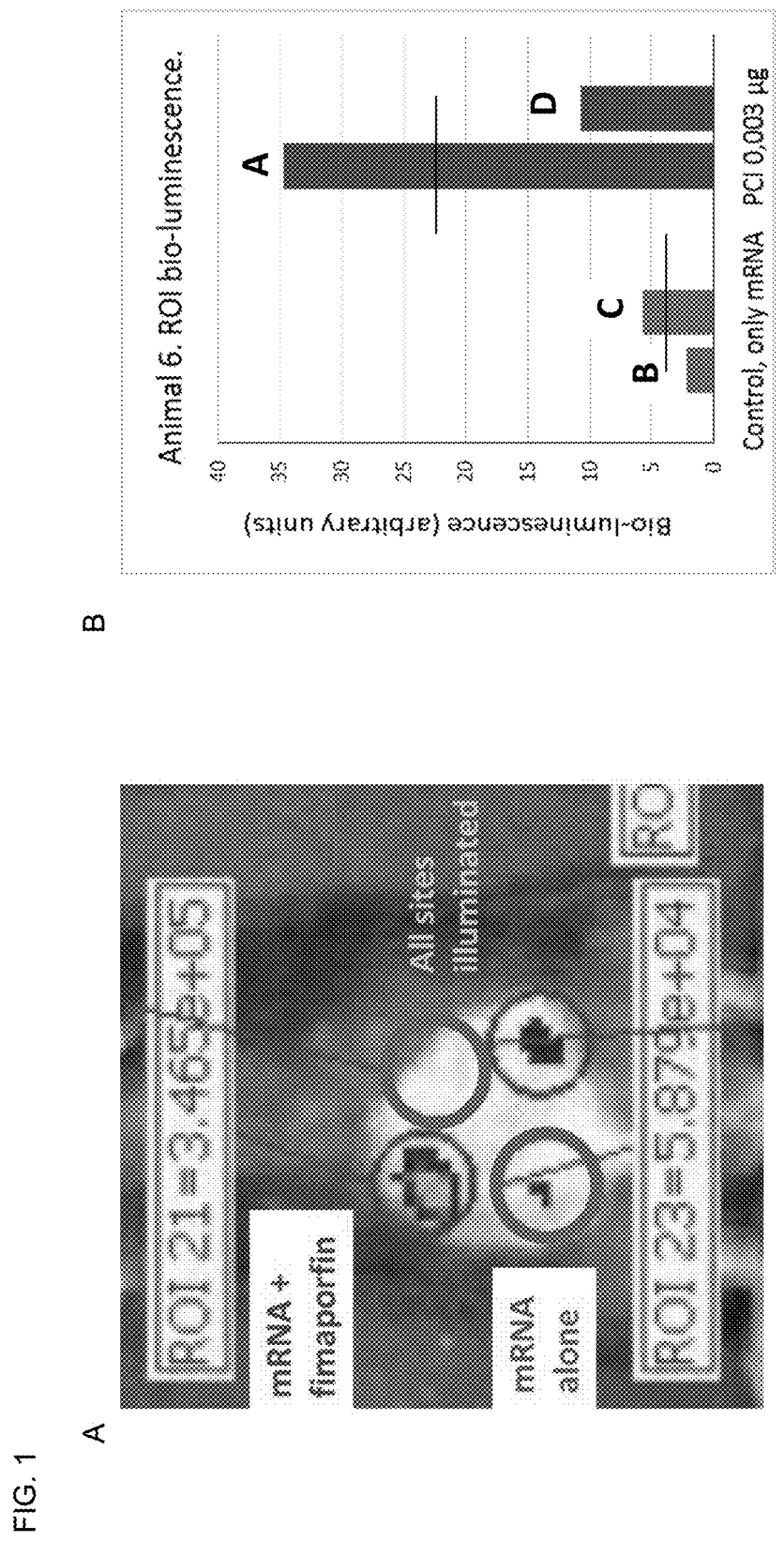

Diken, M. et al., "Selective uptake of naked vaccine RNA by dendritic cells is driven by macropinocytosis and abrogated upon DC maturation", Gene Therapy (2011) vol. 18, pp. 702-708.
Felgner, P.L. et al., "Cationic liposome-mediated transfection", Nature, vol. 337 (Jan. 26, 1989), pp. 387-388.
Fisher, K.J. et al., "The transmembrane domain of diphtheria toxin improves molecular conjugate gene transfer", Biochem. J. (1997), vol. 321, pp. 49-58.
Hecker, J.G. et al., "Nonviral Gene Delivery to the Lateral Ventricles in Rat Brain: Initial Evidence for Widespread Distribution and Expression in the Central Nervous System", Molecular Therapy, vol. 3, No. 3, (Mar. 2001), pp. 375-384.
Høgset, A. et al., "Photochemical internalisation in drug and gene delivery", Advanced Drug Delivery Reviews, vol. 56 (2004), pp. 95-115.
Jorgensen, J.A.L. et al., "Evaluation of Biodegradable Peptide Carriers for Light-Directed Targeting", Nucleic Acid Therapeutics, vol. 23, No. 2 (2013), pp. 131-139.
Kariko, K. et al., "Overexpression of urokinase receptor in mammalian cells following administration of the in vitro transcribed encoding mRNA", Gene Therapy (1999) vol. 6, pp. 1092-1100.
Lu, D. et al., "Optimization of methods to achieve mRNA-mediated transfection of tumor cells in vitro and in vivo employing cationic liposome vectors", Cancer Gene Ther., vol. 1 (1994), pp. 245-252. Abstract only.
Malone, R.W. et al., "Cationic liposome-mediated RNA transfection", Proc. Natl. Acad. Sci. USA, vol. 86, (Aug. 1989), pp. 6077-6081.
Nair, S.K. et al., "Induction of primary carcinoembryonic antigen (CEA)-specific cytotoxic T lymphocytes in vitro using human dendritic cells transfected with RNA", Nature Biotechnology, vol. 16 (Apr. 1998), pp. 364-369.
Ndoye, A. et al., "Eradication of p53-Mutated Head and Neck Squamous Cell Carcinoma Xenografts Using Nonviral p53 Gene Therapy and Photochemical Internalization", Mol. Ther., vol. 13 (2006), pp. 1156-1162.
Oliveira, S. et al., "Photochemical internalization enhances silencing of epidermal growth factor receptor through improved endosomal escape of siRNA", Biochimica et Biophysica Acta 1768 (2007), pp. 1211-1217.
Oliveira, S. et al., "Delivery of siRNA to the Target Cell Cytoplasm: Photochemical Internalization Facilitates Endosomal Escape and Improves Silencing Efficiency, In Vitro and In Vivo", Current Pharmaceutical Design (2008), vol. 14, pp. 3686-3697.
Park, S-J. et al., "The transfection efficiency of photosensitizer-induced gene delivery to human MSCs and internalization rates of EGFP and Runx2 genes", Biomaterials, vol. 33 (2012), pp. 6485-6494.
Sahin, U. et al., "mRNA-based therapeutics—developing a new class of drugs", Nature Reviews Drug Discovery, vol. 13, No. 10 (Oct. 2014), pp. 759-780.
Sahin, U. et al., "Personalized RNA mutanome vaccines mobilize poly-specific therapeutic immunity against cancer", Nature, vol. 547 (2017), pp. 222-226.
Selbo, P.K. et al., "In Vivo Documentation of Photochemical Internalization, a Novel Approach to Site Specific Cancer Therapy", Int. J. Cancer, vol. 92 (2001) pp. 761-766.
Selbo, P.K. et al., "Photochemical internalization provides time- and space-controlled endolysosomal escape of therapeutic molecules", Journal of Controlled Release, vol. 148, No. 1 (2010), pp. 2-12.
Sultan, A.A. et al., "Disulfonated tetraphenyl chlorin (TPCS2a)-induced photochemical internalisation of bleomycin in patients with solid malignancies: a phase 1, dose-escalation, first-in-man trial", Lancet Oncol., vol. 17, No. 9 (2016), pp. 1217-1229.
Warren, L. et al., "Feeder-Free Derivation of Human Induced Pluripotent Stem Cells with Messenger RNA", Scientific Reports, vol. 2, No. 657, pp. 1-7.
Zangi, L. et al., "Modified mRNA directs the fate of heart progenitor cells and induces vascular regeneration after myocardial infarction", Nat. Biotechnol., vol. 31, No. 10 (Oct. 2013), pp. 898-907.

* cited by examiner

A

B

METHOD OF INTRODUCING AN mRNA MOLECULE INTO A CELL

The present invention relates to a method for introducing mRNA into cells in vivo, preferably into the cytosol of cells, using a photosensitising agent and irradiation of the cells with light of a wavelength effective to activate the photosensitising agent, and to the use of this method for expressing polypeptides in the cell, e.g. in therapeutic methods.

mRNA offers the potential as a drug class for various therapeutic purposes including prophylactic and therapeutic vaccination. mRNA-based therapeutics can, in principle, also be used in the treatment of a very large variety of diseases, e.g. in immunotherapy of cancer and other diseases, in regenerative medicine (e.g. CVD, neurodegenerative diseases), cancer (other than immunotherapy), acute infectious diseases and many others. However, the widespread use of mRNA for these purposes has so far been severely hindered by problems with delivering the functional mRNA into cells.

Carriers have been used to attempt to overcome this issue. Among synthetic carriers, the most common way to deliver mRNA molecules has been by the use of cationic lipids (Felgner and Ringold, 1989, *Nature* 337, 387-388; Malone et al., 1989, *Proc Natl Acad Sci USA* 86, 6077-6081; Lu et al., 1994, *Cancer Gene Ther* 1, 245-252; Kariko et al., 1999, *Gene Ther* 6, 1092-1100; Hecker et al., 2001, *Mol Ther* 3, 375-384.). In contrast, there are only a few examples of the use of polycations, such as DEAE-dextran (Malone et al. 1989, supra), poly(L-lysine) (Fisher and Wilson 1997, *Biochem J* 321 (Pt 1), 49-58), dendrimers (Nair et al. 1998, *Nat Biotechnol* 16, 364-369) and polyethylenimine (Bettinger et al. 2001, *Nucleic Acids Res* 29, 3882-389). The most successfully employed lipid vehicle for mRNA delivery is lipofectamine. However, toxic reactions have been observed using lipofectamine in vivo limiting the potential of this agent for clinical applications.

However, there remains a need for methods of delivering mRNA in vivo which are safe, controlled and direct the mRNA to the required location. The present invention provides a method of delivering mRNA in vivo which does not rely on carriers but instead uses a photochemical internalisation method allowing controlled and timed release of the mRNA to the site of interest. It has been found that the method provides superior in vivo delivery of mRNA to target cells relative to the use of lipofectamine as the gold standard for mRNA delivery. This provides a method suitable for various therapeutic applications.

Photochemical internalization (PCI) is a strategy based on light-induced rupture of endocytic membranes, triggered by the use of a photosensitising compound that localizes in these membranes (Berg et al., 1999, *Cancer Res* 59, 1180-1183). Upon illumination, the photosensitising compound initiates an oxidative process by creating reactive oxygen species (ROS) that destroys the membrane.

PCI methods provide a mechanism for introducing molecules into the cytosol of a cell in a manner which does not result in widespread cell destruction or cell death if the methodology is suitably adjusted to avoid excessive toxic species production, e.g. by lowering illumination times or photosensitiser dose. The basic method of photochemical internalisation (PCI), is described in WO 96/07432 and WO 00/54802, which are incorporated herein by reference. In such methods, the molecule to be internalised (which in the present invention would be the mRNA molecule), and a photosensitising agent are brought into contact with a cell. The photosensitising agent and the molecule to be internalised are taken up into a cellular membrane-contained subcompartment within the cell, i.e. they are endocytosed into an intracellular vesicle (e.g. a lysosome or endosome). On exposure of the cell to light of the appropriate wavelength, the photosensitising agent is activated which directly or indirectly generates reactive oxygen species which disrupt the intracellular vesicle's membranes. This allows the internalized molecule to be released into the cytosol. It was found that in such a method the functionality or the viability of the majority of the cells was not deleteriously affected.

The PCI strategy has been used to deliver a variety of molecules into cytosol in vitro, e.g. siRNA molecules (Boe et al., 2007, *Oligonucleotides* 17, 166-173; Oliveira et al., 2007, *Biochim Biophys Acta* 1768, 1211-1217). In vivo, the effect of PCI-mediated therapy on tumour treatment has been documented with bleomycin (Berg et al., 2005, *Clin Cancer Res* 11, 8476-8485), the protein toxin gelonin (Selbo et al., 2001, *Int J Cancer* 92, 761-766) and with a plasmid encoding a therapeutic gene (Ndoye et al., 2006 *Mol Ther* 13, 1156-1162) PCI has been developed for use to treat several types of tumours (Selbo et al., 2010, *J. Control. Release,* 148(1), 2-12; and Hogset A, et al., 2004, *Adv. Drug Deliver. Rev.,* 56(1), 95-115), and is currently in clinical development for this purpose using bleomycin as the active agent (Sultan et al., 2016, *Lancet Oncol.* 17(9):1217-1229.

PCI has been used for delivery of oligonucleotides (Hogset et al., 2004, *Adv Drug Deliv Rev,* 56, 95-115). Whilst the use of PCI methods to internalize molecules of interest, including oligonucleotides such as mRNA has been suggested (WO96/07432), the use of PCI to internalize mRNA presents particular problems and it has been found that, when tested, normal PCI techniques are not effective at internalizing mRNA. mRNA and related molecules such as siRNA have been internalized with PCI, but by using carriers (WO2008/007073 and Boe and Hovig, 2013, *Methods Mol. Biol.,* 969: 89-100).

In the work leading to the present invention, a specific and new protocol for light-induced mRNA delivery resulting in site-specific protein production has been developed. We show for the first time that potent light-induced protein production is achievable by combining mRNA transfection and PCI. Importantly, we have developed a protocol that is controllable in a time- and site-specific manner. Furthermore, the method avoids the use of transfection agents and the side effects caused by those agents.

The method of the invention is particularly advantageous because it is not a complex method and may be used with a variety of mRNA molecules and target cells/locations. Furthermore, the timing and location of irradiation to release the molecules may be controlled such that it is released only at the time and location that is desired to achieve the required effects. As such, exposure of cells to the various components is minimised, and undesirable side effects are minimised. This is in contrast to the standard techniques for mRNA delivery, where it is not possible to control the timing and location of the release of the various components without the use of targeting agents (which add a further level of complexity).

As described in the Examples herein, a specific protocol has been developed in which very low levels of photosensitiser (approximately 25 to 25,000 times lower than in standard protocols) is used to achieve mRNA delivery. To the best of our knowledge, this is the first teaching of successful (naked) mRNA delivery in vivo using a PCI method.

Thus, in a first aspect, the invention provides an in vivo method for introducing an mRNA molecule into the cytosol of a cell(s) in a subject, said method comprising
  i) contacting said cell(s) with an mRNA molecule and a photosensitising agent, and
  ii) irradiating the cell(s) with light of a wavelength effective to activate the photosensitising agent,
  wherein said photosensitising agent is a sulphonated meso-tetraphenyl chlorin, sulfonated tetraphenylporphine or a di- or tetrasulfonated aluminium phthalocyanine used in an amount of 0.0001 to 1 µg. Once activated, intracellular compartments within said cell containing said photosensitising agent release mRNA contained in these compartments into the cytosol where the mRNA may be expressed.

As referred to herein said "mRNA" molecule is a polymer of ribonucleotides, each containing the sugar ribose in association with a phosphate group and a nitrogenous base (typically, adenine, guanine, cytosine, or uracil). Modified molecules may be used, e.g. with modified backbones or non-naturally occurring nucleotides or naturally occurring modified nucleotides such as pseudouridine, 2-thiouridine, 5-methyluridine, 5-methylcytidine or N6-methyladenosine, so as to increase their half life providing this does not affect their functionality. Thus, the term "mRNA" thus also includes such modified molecules, i.e. encompasses derivatives or variants of mRNA which exhibit the same function, i.e. interaction with a ribosome and translation to express an encoded sequence. Preferred variants include those in which a modified backbone has been used (as above) or one or more non-naturally occurring bases or naturally occurring modified nucleotides (which may be introduced during synthesis) is used.

As is the case for DNA, RNA can form complementary hydrogen bonds, and RNA may be double-stranded (dsRNA), single-stranded (ssRNA) or double-stranded with a single-stranded overhang. Preferably the mRNA used in accordance with the invention is single stranded. The single stranded molecule may form tertiary structures which include double stranded regions, e.g. hairpin structures formed through internal base-pairing. Preferably the mRNA has a 5' cap and a 3' poly(A) tail (e.g. 120-150 nucleotides in length). Flanking untranslated regions may be present at the 3' and/or 5' end. Preferably, said mRNA molecules are 50-10,000 nucleotides long, more preferably 50-1000 or 1000-5000, e.g. 100-500 or 1500-2500 nucleotides long (when considering the sense strand).

The mRNA is not associated with a carrier or other molecule, i.e. is not bound or conjugated to or carried by any other component to aid its internalization. Such association includes any connection whether by binding, steric entrapment or other method that connects the molecules together so that they would remain associated under appropriate conditions. Thus no transfection agent or carrier is used. In this sense, the mRNA that is used is naked, i.e. free of associated molecules affecting its internalization. The photosensitising agent that is used with the mRNA in methods described herein does not constitute a carrier or transfection agent for the mRNA.

Preferably the mRNA encodes a polypeptide, i.e. carries sufficient consecutive coding codons that if translated would form a polypeptide. The polypeptide may include a signal peptide to allow processing and/or transport once translated. The polypeptide may comprise a single functional entity or contain multiple functional entities, e.g. the polypeptide may contain one or more peptide antigens, which may be used for vaccination. The mRNA may encode more than one polypeptide such that the result of translation is more than one polypeptide. Non-coding, e.g. stop codons, may also be present in the mRNA molecule. As referred to herein the "polypeptide" (which encompasses a peptide) comprises at least 5 consecutive amino acids. In a preferred aspect the polypeptide is at least 10, 20 or 30 amino acids in length, and less than 3000, 2000, 1000, 700, 500, 200 or 100 amino acids in length e.g. from 10-100, 200, 500, 700, 1000, 2000 or 3000 amino acids in length.

In a preferred aspect the polypeptide is expressed in the cell. The mRNA once internalized into the cell is bound by a ribosome and the mRNA translated into an amino acid sequence using the cell's gene expression machinery. The polypeptide is preferably a therapeutic molecule, i.e. a polypeptide with therapeutic properties such as a vaccine polypeptide, an antibody, an enzyme, a cytokine, a growth factor or a peptide hormone, for example.

The method may be used to introduce more than one type of mRNA molecule into a cell. In other words, mRNA molecules having different sequences can be introduced simultaneously into a cell. The molecules they express may act in different ways or interact with one another.

Appropriate methods for preparing mRNAs are known in the art and include chemical synthesis, in vitro transcription, mRNA expression vectors, and PCR expression cassettes. Such techniques are well known in the art. See for example Pon et al., 2005, *Nucleosides Nucleotides Nucleic Acid.* 24(5-7), 777-81, Du et al., 2006, *Biochem. Biophys. Res. Commun.* 345(1), 99-105 and Katoh et al., 2003, *Nucleic Acids Res Suppl.* (3), 249-50, Sahin et al., 2014, *Nat. Rev. Drug Discov.*, 13(10), 759-780. mRNA for use in the invention may also be isolated from cells or tissues. In particular this allows personalized treatment, e.g. using mRNA isolated from the tumour of a subject to allow expression of patient specific tumour antigens in cancer immunotherapy.

The method of the invention achieves translocation of the mRNA molecule into the cytosol. It will be appreciated however that uptake of each and every molecule contacted with the cell is not achievable. Significant and improved uptake relative to background levels in which no PCI is used is however achievable.

Preferably methods of the invention allow the uptake of mRNA molecules at sufficient levels that their effect is evident in the expressed products of those cells.

The appropriate concentration of mRNA to be contacted with the cell may be adjusted to achieve this aim, e.g. to achieve expression of the encoded sequence to desired levels after incubation with cells for e.g. 24, 48, 72 or 96 hours (e.g. 24 to 48 hours). The photosensitising agent type and/or concentration and the irradiation time can also be adjusted to achieve the expression required.

As used herein "and/or" refers to one or both (or more) of the recited options being present, e.g. A, B and/or C includes the options i) A, ii) B, iii) C, iv) A and B, v) A and C, vi) B and C, and vii) A, B and C.

Levels of expression can be measured by determining the level of protein in the cell, using standard techniques known in the art such as Western Blotting.

Expression may be assessed relative to expression achieved without the use of PCI. Comparisons can be made between the levels of protein expression that are seen at a certain mRNA (and/or photosensitiser) concentrations, in the presence and absence of PCI. For example, the method of the invention, including the therapeutic method, preferably allows enhanced expression of polypeptides of at least 10%, e.g. at least 20, 30, 40, 50, 60, 70, 80 or 90% or higher e.g. at least 100, 200, 300, 400 or 500%, compared to polypeptide expression achieved by carrying out the method in the absence of the irradiation step of the PCI technique. In a particularly preferred aspect, the method of the invention improves expression relative to delivery using lipofectamine without PCI by at least 10%, e.g. at least 20, 30, 40, 50, 60, 70, 80 or 90% or higher e.g. at least 100, 200, 300, 400 or 500%. Conveniently, the encoded polypeptide is expressed such that amounts of 1-100 μg are produced in the subject. Such amounts are sufficient for vaccination and immunotherapy. Larger amounts may generated, e.g. 1-100 mg when the polypeptide is used for direct therapeutic purposes, e.g. in protein therapy methods.

The "cell" or "cells" are in a body. The term "cell" or "cells" is used interchangeably herein. Thus the cell is provided within a subject or organism, i.e. an in vivo cell. The term "cell" include all eukaryotic cells (including insect cells and fungal cells). Representative "cells" thus include all types of mammalian and non-mammalian animal cells, plant cells, insect cells, fungal cells and protozoa. Preferably however the cells are mammalian, for example cells from monkeys, cats, dogs, horses, donkeys, sheep, pigs, goats, cows, mice, rats, rabbits, guinea pigs, but most preferably from humans. In the alternative the cells may be piscine cells.

When used in vivo the "subject" refers to a mammal, reptile, bird, insect or fish. Preferably the subject is a mammal, particularly a primate (preferably a human), domestic or companion animal, livestock or laboratory animal. In an alternative preferred aspect the subject is a fish. Thus preferred animals include mice, rats, rabbits, guinea pigs, cats, dogs, monkeys, pigs, cows, goats, sheep, donkeys, horses and fish.

As used herein "contacting" refers to bringing the cells and the photosensitising agent and/or mRNA into physical contact with one another under conditions appropriate for internalization into the cells, e.g. preferably at 37° C. in an appropriate nutritional medium, e.g. from 25-39° C. Conveniently in preferred methods the contact occurs in vivo. Preferred methods of performing the invention including the timing and options for the contacting step are discussed hereinafter.

The photosensitising agent is an agent which is activated on illumination at an appropriate wavelength and intensity to generate an activated species. Conveniently such an agent may be one which localises to intracellular compartments, particularly endosomes or lysosomes. A range of such photosensitising agents are known in the art and are described in the literature, including in WO96/07432, which is incorporated herein by reference. In accordance with the invention, the photosensitising agent which is used is a sulphonated meso-tetraphenyl chlorin, sulfonated tetraphenylporphine or a di- or tetrasulfonated aluminium phthalocyanine.

In a preferred aspect the meso-tetraphenyl chlorin is $TPCS_{2a}$ (tetraphenyl chlorin disulfonate) or $TPBS_{2a}$ (tetraphenyl bacteriochlorin disulfonate), the sulfonated tetraphenylporphine is $TPPS_n$, e.g. $TPPS_4$ or $TPPS_{2a}$ (tetraphenylporphine sulfonate or disulfonate), and the di- or tetrasulfonated aluminium phthalocyanine is $AlPcS_{2a}$ (aluminium phthalocyanine disulfonate). Pharmaceutically acceptable salts thereof may be used.

Particularly preferred are $TPCS_{2a}$ and $TPPS_{2a}$, the structures of which are provided below.

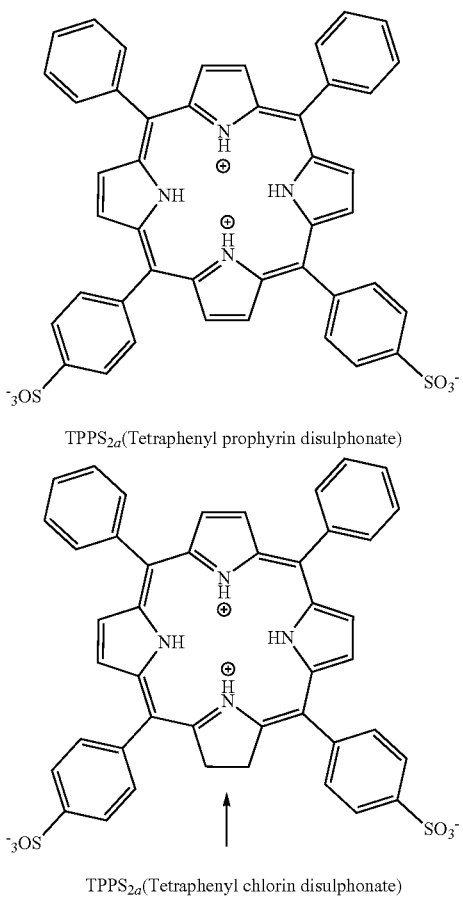

$TPPS_{2a}$(Tetraphenyl prophyrin disulphonate)

$TPPS_{2a}$(Tetraphenyl chlorin disulphonate)

The arrow indicates the structural difference between the two molecules.

Optionally, the photosensitising agent may be attached to or associated with or conjugated to one or more carrier molecules or targeting molecules which can act to facilitate or increase the uptake of the photosensitising agent. Thus the photosensitising agent may be linked to a carrier. For example, the photosensitising agent may be provided in the form of a conjugate, e.g. a chitosan-based conjugate, for example a conjugate disclosed in WO2013/189663, which is hereby incorporated by reference.

Whilst location specificity may be achieved by local delivery and activation by irradiation at the site of interest, if desired, the photosensitising agent may be targeted to specific cells (e.g. cancer cells) or tissues, by being associated or conjugated to specific targeting molecules that will promote the specific cellular uptake of the photosensitising agent molecule into desired cells or tissues.

Many different targeting molecules can be employed, e.g. as described in Curiel, 1999, *Ann. New York Acad. Sci.* 886, 158-171; Bilbao et al., 1998, in Gene Therapy of Cancer (Walden et al., eds., Plenum Press, New York); Peng and Russell, 1999, *Curr. Opin. Biotechnol.* 10, 454-457; Wickham, 2000, *Gene Ther.* 7, 110-114.

"Irradiation" of the cell to activate the photosensitising agent refers to the administration of light directly or indirectly as described hereinafter. Thus cells may be illuminated with a light source for example directly or indirectly, e.g. in vivo when the cells are below the surface of the skin or are in the form of a layer of cells not all of which are directly illuminated, i.e. without the screen of other cells. Preferred methods of irradiation are as described hereinafter.

Conveniently, the method may be carried out as now described. Where a carrier is to be used for the photosensitising agent, the carrier may be associated, bound or conjugated to the photosensitising agent by simply mixing the two components under appropriate conditions and concentrations and allowing the components to interact. The conditions under which this contacting step is carried out, and appropriate concentrations for each the carrier and the photosensitising agent can readily be determined by the person skilled in the art by carrying out routine testing.

In the method of the invention, the mRNA molecule and the photosensitising agent (optionally with a carrier and/or a targeting molecule) are applied simultaneously, separately or sequentially to the cells, whereupon the photosensitising agent and the mRNA molecule are endocytosed or in other ways translocated into endosomes, lysosomes or other intracellular membrane restricted compartments.

The mRNA molecule and the photosensitising compound may be applied to the cells together or sequentially. Conveniently the mRNA is administered to the cell simultaneously with the photosensitising agent (though they may be administered separately, e.g. sequentially). The mRNA molecule and the photosensitising agent may be taken up by the cell into the same or different intracellular compartments (e.g. they may be co-translocated).

The mRNA is then released by exposure of the cells to light of suitable wavelengths to activate the photosensitising agent which in turn leads to the disruption of the intracellular compartment membranes and the subsequent release of the mRNA, which may be located in the same compartment as the photosensitising agent, into the cytosol. Thus, in these methods the final step of exposing the cells to light results in the mRNA being released from the same intracellular compartment as the photosensitising agent and becoming present in the cytosol.

WO 02/44396 (which is incorporated herein by reference) describes a method in which the order of the steps could be changed such that, for example, the photosensitising agent is contacted with the cells and activated by irradiation before the molecule to be internalised (in this case mRNA) is brought into contact with the cells. This adapted method takes advantage of the fact that it is not necessary for the molecule to be internalised to be present in the same cellular subcompartment as the photosensitising agent at the time of irradiation.

Thus in a preferred embodiment, said photosensitising agent and said mRNA molecule are applied to the cell together, or said photosensitising agent is applied separately relative to said mRNA molecule. As a consequence they may be taken up by the cell into the same intracellular compartment and said irradiation may then be performed. This is referred to as a "light after" method.

In an alternative embodiment, said method can be performed by contacting said cell with a photosensitising agent, contacting said cell with the mRNA molecule to be introduced and irradiating said cell with light of a wavelength effective to activate the photosensitising agent, wherein said irradiation is performed prior to the cellular uptake of said mRNA molecule into an intracellular compartment containing said photosensitising agent, preferably prior to cellular uptake of said mRNA molecule into any intracellular compartment.

Said irradiation can be performed after the cellular uptake of the mRNA molecule into an intracellular compartment, whether or not the mRNA molecule and the photosensitising agent are localised in the same intracellular compartments at the time of light exposure. In one preferred embodiment however irradiation is performed prior to cellular uptake of the molecule to be internalised (mRNA molecule). This is the so-called "light before" method.

"Internalisation" as used herein, refers to the cytosolic delivery of molecules. In the present case "internalisation" thus includes the step of release of molecules from intracellular/membrane bound compartments into the cytosol of the cells.

As used herein, "cellular uptake" or "translocation" refers to one of the steps of internalisation in which molecules external to the cell membrane are taken into the cell such that they are found interior to the outer lying cell membrane, e.g. by endocytosis or other appropriate uptake mechanisms, for example into or associated with intracellular membrane-restricted compartments, for example the endoplasmic reticulum, Golgi body, lysosomes, endosomes etc.

The step of contacting the cells with a photosensitising agent and with the mRNA molecule may be carried out in any convenient or desired way. As discussed above, these agents may be applied to cells together, separately, simultaneously or sequentially.

The photosensitising agent is brought into contact with the cells at an appropriate concentration and for an appropriate length of time which can easily be determined by a skilled person using routine techniques and will depend on such factors as the particular photosensitising agent used, the mode of administration, the target cell type and location, the course of treatment, the age and weight of the patient/subject, the medical indication, the body or body area to be treated and may be varied or adjusted according to choice. The concentration of the photosensitising agent must be such that once taken up into the cell, e.g. into, or associated with, one or more of its intracellular compartments and activated by irradiation, one or more cell structures are disrupted e.g. one or more intracellular compartments are lysed or disrupted.

The photosensitising agent is used in an amount of 0.0001 to 1 µg (or 0.5 µg), preferably 0.001 (or 0.0001) to 0.1 µg. Other preferred ranges include 0.0001-0.01 µg. This is considerably lower than amounts used routinely for PCI such as 25 µg. It will be noted from FIG. 3 that use of amounts above 1 µg adversely affect mRNA delivery, indeed they have a negative effect relative to control. The dose may be selected depending on the mode of administration and the light dose. For example, for intradermal administration a dose of 0.0001 to 0.05 µg may be selected (e.g. 0.001 to 0.01 µg). The same or higher doses may be used for intratumoural delivery, e.g. a dose of 0.001 to 1.0 µg (e.g. 0.01 to 0.2 µg) may be selected. The above described dose may be used for local delivery to small local areas (less than a cubic cm). When larger areas are to be treated, the dose may be scaled accordingly.

The photosensitising agent is conveniently provided in a solution with a concentration of 0.005 to 200 µg/ml, preferably 0.05 to 20 µg/ml. This concentration is suitable for local delivery.

Similar considerations apply to the mRNA. The mRNA is preferably used in an amount of 0.1 to 100 µg, e.g. 1 to 10 µg. The dose may be selected depending on the mode of administration as discussed above. The above described dose may be used for local delivery to small local areas (less than a cubic cm). When larger areas are to be treated, the dose may be scaled accordingly. The RNA is conveniently provided in a solution with a concentration of 5 to 5000 μg/ml, preferably 50 to 500 μg/ml. This concentration is suitable for local delivery.

An appropriate concentration should also take into account the mRNA molecule and photosensitising agent in question, the cells in question and the final concentration it is desired to achieve in the cells. An increased contact time usually results in increased uptake of the molecule in question. However, shorter incubation times, for example 30 minutes to 1 hour, can also result in an improved specificity of the uptake of the molecule. Thus, in selecting a contact time for any method, an appropriate balance must be struck between obtaining a sufficient uptake of the molecule while maintaining sufficient specificity of the PCI treatment.

The time of incubation of the cell(s) with the photosensitising agent (i.e. the "contact" time) can vary from a few minutes to several hours, e.g. from 30 minutes to 4 hours, preferably from 45 to 90 minutes. Alternatively, longer incubations may be used such as for up to 2, 5, 10, 12, 18 or 24 hours. The time of incubation should be such that the photosensitising agent is taken up by the appropriate cells, e.g. into intracellular compartments in said cells.

The mRNA molecule is brought into contact with the cells at an appropriate concentration and for an appropriate length of time. Appropriate concentrations are as discussed above. Contact times are as discussed above for the photosensitising agent.

As mentioned above, it has been found that the contact may be initiated even several hours after the photosensitising agent has been added and irradiation taken place. However, conveniently, the mRNA and photosensitising agent are contacted with the cell(s) at the same time for the contact times indicated above, prior to irradiation.

To achieve an appropriate time of incubation (or contact time) by which the mRNA molecule and photosensitising agent are brought into contact with the target cells in vivo will be dependent on factors such as the mode of administration and the type of mRNA molecule and photosensitising agent. For example, if the mRNA molecule is injected into a tumour, tissue or organ which is to be treated, the cells near the injection point will come into contact with and hence tend to take up the mRNA molecule more rapidly than the cells located at a greater distance from the injection point, which are likely to come into contact with the mRNA molecule at a later time point and lower concentration.

In addition, an mRNA molecule administered some way distant from the cells of interest may take some time to arrive at the target cells and it may thus take longer post-administration e.g. several hours or days, in order for a sufficient or optimal amount of the mRNA molecule to accumulate in a target cell or tissue. The same considerations of course apply to the time of administration required for the uptake of the photosensitising agent into cells. The time of administration required for individual cells in vivo is thus likely to vary depending on these and other parameters.

Nevertheless, although the situation in vivo is more complicated than if the method were used in vitro, the underlying concept is that the time at which the molecules come into contact with the target cells must be such that before irradiation occurs an appropriate amount of the photosensitising agent has been taken up by the target cells and either: (i) before or during irradiation the mRNA molecule has either been taken up, or will be taken up after sufficient contact with the target cells, into the same or different intracellular compartments or (ii) after irradiation the mRNA molecule is in contact with the cells for a period of time sufficient to allow its uptake into the cells. Provided the mRNA molecule is taken up into intracellular compartments affected by activation of the photosensitising agent (e.g. compartments in which the agent is present), the mRNA molecule can be taken up before or after irradiation. Conveniently local administration for in vivo applications are contemplated and thus the contact times indicated hereinbefore are appropriate. For the avoidance of doubt, contact time refers to the period of time in which the agent(s) is in direct contact with the target cell. The time of administration may precede the time of contact as the agent(s) makes its way to the target cells. When local administration is used direct contact begins immediately or shortly after administration.

Illumination of the cell or subject may occur approximately 30 minutes to 48 hours after administration of the various components for use in the method as defined herein. When using local administration for the in vivo methods, illumination may occur from, for example 30 minutes to 4 hours after administration (as contact begins immediately), whereas in in vivo methods in which local administration is not used a longer time after administration may be required if contact time with the target cells within the subject is not immediate (depending on the route of administration), e.g. from 30 minutes to 24 (or 48) hours after administration. In a preferred embodiment the contact time and the time from administration to irradiation are the same, i.e. contact commences immediately on administration.

The light irradiation step to activate the photosensitising agent may take place according to techniques and procedures well known in the art. The dose, wavelength and duration of the illumination must be sufficient to activate the photosensitising agent, i.e. to generate reactive species. Suitable light sources are well known in the art.

The wavelength of light to be used is selected according to the photosensitising agent to be used. Light of a wavelength effective to activate the photosensitising agent is able to elicit the production of reactive oxygen species on exposure of the photosensitising agent to that light. Suitable artificial light sources are well known in the art, e.g. using blue (400-475 nm) or red (620-750 nm) wavelength light. For $TPCS_{2a}$, for example, a wavelength of between 400 and 500 nm, more preferably between 400 and 450 nm, e.g. from 400-435 nm or 420-435 nm, and even more preferably approximately 435 nm, or 435 nm may be used. In the alternative, red light may be used to ensure deeper light penetration, e.g. for tumour tissue. In this case a wavelength of 620-750, e.g. 640-660 nm may be used. Where appropriate the photosensitiser, e.g. a porphyrin or chlorin, may be activated by green light, for example the KillerRed (Evrogen, Moscow, Russia) photosensitiser may be activated by green light.

Suitable light sources are well known in the art, for example the LumiSource® lamp of PCI Biotech AS. Alternatively, an LED-based illumination device which has an adjustable output power of up to 60 mW and an emission spectra of 400-435 nm may be used. For red light, a suitable source of illumination is the PCI Biotech AS 652 nm laser system SN576003 diode laser, although any suitable red light source may be used.

Appropriate light doses can be selected by a person skilled in the art and again will depend on the photosensitising agent and the amount of photosensitising agent accumulated in the target cells or tissues. For example, the light dose typically used for photodynamic treatment of cancers with the photosensitiser Photofrin and the protoporphyrin precursor 5-aminolevulinic acid is in the range 50-150 $J/cm^2$ at a fluence range of less than 200 $mW/cm^2$ in order to avoid hyperthermia. The light doses are usually lower when photosensitising agents with higher extinction coefficients in the red area of the visible spectrum are used. However, for treatment of non-cancerous tissues with less photosensitiser accumulated the total amount of light needed may be substantially higher than for treatment of cancers. Furthermore, if cell viability is to be maintained, the generation of excessive levels of toxic species is to be avoided and the relevant parameters may be adjusted accordingly.

Appropriate light doses can be selected by a person skilled in the art and again will depend on the photosensitising agent used and the amount of photosensitising agent accumulated in the target cell(s) or tissues. The light doses are usually lower when photosensitisers with higher extinction coefficients (e.g. in the red area, or blue area if blue light is used, depending on the photosensitiser used) of the visible spectrum are used. For example, a light dose in the range of 0.24-7.2 $J/cm^2$ at a fluence range of 0.05-20 $mW/cm^2$, e.g. 2.0 $mW/cm^2$, may be used when an LED-based illumination device which has an adjustable output power of up to 60 mW and an emission spectra of 400-435 nm or 420-435 nm is employed. Alternatively, e.g. if the LumiSource® lamp is employed a light dose in the range of 0.1-6 $J/cm^2$ at a fluence range of 0.1-20 (e.g. 13 as provided by Lumisource®) $mW/cm^2$ is appropriate. For red light, a light dose of 0.03-8 $J/cm^2$, e.g. 0.03-4 $J/cm^2$, e.g. 0.3 $J/cm^2$, at a fluence range of 0.1-5 $mW/cm^2$, e.g. 0.81 $mW/cm^2$, may be used.

Conveniently, the light source and irradiation time is selected such that the cell(s) is irradiated with a light dose of from 0.01 to 50 $J/cm^2$, such as 0.1 to 10 $J/cm^2$, e.g. 0.4 to 5 $J/cm^2$ with a 13 $mW/cm^2$ fluence rate.

The time for which the cells are exposed to light in the methods of the present invention may vary. The efficiency of the internalisation of the mRNA molecule into the cytosol increases with increased exposure to light to a maximum beyond which cell damage and hence cell death increases.

A preferred length of time for the irradiation step depends on factors such as the target, the photosensitising agent, the amount of the photosensitising agent accumulated in the target cells or tissue and the overlap between the absorption spectrum of the photosensitising agent and the emission spectrum of the light source. Generally, the length of time for the irradiation step is in the order of minutes to hours, e.g. preferably up to 60 minutes e.g. from 15 seconds to 60 minutes, preferably from 0.5 to 12 minutes, preferably for 4 to 6 minutes.

The methods of the invention may inevitably give rise to some cell killing by virtue of the photochemical treatment i.e. through the generation of toxic species on activation of the photosensitising agent. Depending on the proposed use, this cell death may not be of consequence and may indeed be advantageous for some applications (e.g. cancer treatment). Preferably, however, cell death is avoided to allow translation of the mRNA and expression of the encoded polypeptide. The methods of the invention may be modified such that the fraction or proportion of the surviving cells is regulated by selecting the light dose in relation to the concentration of the photosensitising agent. Again, such techniques are known in the art.

In applications in which viable cells are desirable, substantially all of the cells, or a significant majority (e.g. at least 50%, more preferably at least 60, 70, 80 or 90% of the cells) are not killed. Cell viability following PCI treatment can be measured by standard techniques known in the art such as the MTS test.

Regardless of the amount of cell death induced by the activation of the photosensitiser, for the mRNA molecule to have an effect in the cells, it is important that the light dose is regulated such that some of the individual cells wherein the PCI effect is manifested are not killed by the photochemical treatment alone (although they may subsequently be killed by molecules introduced into the cells if those molecules have a cytotoxic effect).

Cytotoxic effects may be achieved by using, for example, an mRNA molecule which is internalized into a tumour cell by the method of the invention and which by expresses a cytotoxic molecule.

The methods of the invention are used in vivo for various purposes including expression of specific gene products e.g. in protein therapy, immunotherapy and gene therapy methods.

Thus the present invention provides an in vivo method of expressing a polypeptide in a cell(s) in a subject by introducing an mRNA molecule into a cell(s) by a method as defined hereinbefore, wherein said mRNA molecule encodes said polypeptide.

These methods may be used to alter the expression profile of cells or to determine the influence of expression of a particular gene, and/or for therapeutic purposes.

The methods of the invention may also be used in treating any disease, disorder or infection which benefits from expression of a polypeptide, e.g. by expression of one or more genes to provide therapeutic molecules which act directly or indirectly. Such molecules may act directly to provide a therapeutic result or may act indirectly, e.g. by generating an immune response or aiding alteration of gene expression and thus provide gene therapy to a subject, as discussed in more detail hereinafter. Such therapeutic molecules include therapeutic antibodies (or antigen-binding fragments thereof) that may be targeted to appropriate sites to treat diseases, infections or disorders. The therapeutic molecule may also be an enzyme or other functional molecule required for metabolism, e.g. growth factors, cytokine or peptide hormones. Alternatively an inhibitor or cell death inducing molecule may be used, e.g. a cytotoxic molecule. Conveniently, the expressed polypeptide may provide an antigenic molecule against which an immune response may be generated, e.g. for prophylactic or therapeutic vaccination. The immune response may be generated against pathogenic infections, e.g. bacterial or viral infections or against aberrant cells in the body, e.g. cancer cells. Thus the polypeptide may be an antigenic molecule such as a cancer vaccine or a bacterial or viral antigen. Preferred uses of the invention are discussed in more detail hereinbelow.

The invention provides compositions suitable for the therapeutic uses. Thus, the invention provides a pharmaceutical composition comprising an mRNA molecule and a photosensitising agent, wherein said photosensitising agent is a sulphonated meso-tetraphenyl chlorin, sulfonated tetraphenylporphine or a di- or tetrasulfonated aluminium phthalocyanine and is provided in the amount of 0.0001 to 1 μg. Also provided is the composition for use in therapy. Preferably said photosensitising agent and/or said mRNA is as defined hereinbefore. A pharmaceutical composition comprises in addition to the active ingredient(s) one or more pharmaceutically acceptable diluents, carriers or excipients.

Alternatively the mRNA and photosensitising agent may be in separate solutions or compositions allowing different mechanisms or timings for administration or application. As referred to herein "co-administration" and "co-application" refers to use of both components in the same method rather than simultaneous use (either in terms of timing or in the same composition).

Alternatively, the present invention provides a kit comprising an mRNA molecule and a photosensitising agent as described herein. Preferably said kit (or product) is for simultaneous, separate or sequential use in a medical treatment.

The invention further provides an mRNA molecule and a photosensitising agent for use in treating or preventing a disease, disorder or infection in a subject by expressing a polypeptide encoded by said mRNA molecule, wherein said photosensitising agent is a sulphonated meso-tetraphenyl chlorin, sulfonated tetraphenylporphine or a di- or tetrasulfonated aluminium phthalocyanine used in an amount of 0.0001 to 1 µg. Preferably the photosensitising agent and/or said mRNA is as defined hereinbefore.

The intended treatment or prevention is preferably carried out using a method as described hereinbefore.

In an alternative description of the invention, the present invention provides the use of an mRNA molecule and a photosensitising agent in the preparation of a medicament for treating or preventing a disease, disorder or infection in a subject by expressing a polypeptide encoded by said mRNA molecule, wherein said photosensitising agent is a sulphonated meso-tetraphenyl chlorin, sulfonated tetraphenylporphine or a di- or tetrasulfonated aluminium phthalocyanine used in an amount of 0.0001 to 1 µg. Preferably said photosensitising agent and/or said mRNA are as defined herein. Preferably said cells are subject to a method as described herein.

Optionally said medicament may contain only one of said mRNA molecule and photosensitising agent and may be used in methods in which said mRNA molecule or photosensitising agent which is not present in said medicament is for administration to said patient (or subject) when treating or preventing said disease, disorder or infection.

In a further alternative description of the invention, the present invention provides a method of treating or preventing a disease, disorder or infection in a subject comprising introducing an mRNA molecule into one or more cells in vivo in said subject according to the methods as defined herein.

As defined herein "treatment" refers to reducing, alleviating or eliminating one or more symptoms of the disease, disorder or infection which is being treated, relative to the symptoms prior to treatment. "Prevention" (or preventing or prophylaxis) refers to delaying or preventing the onset of the symptoms of the disease, disorder or infection. Prevention may be absolute or may be effective only in some individuals, or cells, or for a limited amount of time.

The disease, disorder or infection to be treated or prevented may be any condition which would benefit from the expression of one or more polypeptides. Such conditions may exhibit low or no expression of the polypeptide, e.g. when the endogenous polypeptide is not expressed at required levels, is absent or higher levels would be therapeutic (e.g. to correct metabolic processes or for vaccination), or would benefit from use of an exogenous polypeptide for therapeutic purposes, e.g. for vaccination or to achieve cell death, e.g. a cytotoxic molecule. In another aspect, and as described hereinafter, the therapy may be gene therapy. In some instances the gene therapy may provide a gene to replace a defective or missing equivalent in the subject. The expressed polypeptides may act directly in a therapeutic manner (e.g. a cytotoxic molecule) or may initiate a therapeutic response, e.g. a therapeutic immune response. Particularly preferred diseases, disorders or infections to be treated include cancer, cardiovascular disease, autoimmune diseases, cystic fibrosis, neurodegenerative diseases such as Huntington's disease, Alzheimer's disease and Parkinson's disease, viral infections such as influenza, hepatitis (e.g. B and C), HIV and herpes, infections with intracellular or extracellular bacteria, such as in tuberculosis, leprosy, chlamydia, listeria, legionella and cholera and infection by E. coli, P. aeruginosa, S. aureus, Streptococcus spp., N. meningitidis and S. pyogenes, infections by parasites, e.g. in malaria and leishmaniosis and other diseases, disorders or infections discussed herein.

The in vivo uses may be divided into protein therapy, immunotherapy and gene therapy methods.

In protein therapy methods, the mRNA is used to produce a protein that the patient is lacking, e.g. because of an inherited mutation or reduced expression, or which would have a therapeutic effect. In one alternative, this could be e.g. an enzyme, a peptide hormone, a cytokine, a growth factor, a blood clotting factor (in bleeding disorders) or other important proteins. In this case an mRNA encoding the missing protein is delivered to suitable cells in the body (for example in the skin, muscle, liver etc.) so that these cells produce the missing protein that will either act inside the producer cell (e.g. if the mRNA encodes an intracellular enzyme), locally (e.g. to produce a growth factor in a certain tissue) or systemically (e.g. to produce a missing blood clotting factor or a peptide hormone).

In a second alternative, the protein may be a protein which has a therapeutic effect, but is not necessarily naturally occurring. For example, the mRNA may encode one or more antibodies to an infectious agent. In this case, upon delivery of the mRNA to the body (into any tissue capable of producing the antibody protein and secreting it into the blood stream) the body will rapidly (4-6 hours) synthesize antibodies to the infectious agent that may rapidly stop the development of the infection. Such therapy will be very specific to the specific infectious agent, and will not be subject to problems e.g. with antibiotic resistance. Preferably this method may be used to treat acute infections (until the body's immune system can take over) resulting from pathogens, e.g. viruses, bacteria (particularly extracellular but also intracellular bacteria) and parasites. The method may also be used to supplement the body's immune response to treat various diseases, disorders or infections, including viral diseases such as influenza, hepatitis (e.g. B and C), HIV and Herpes and many other viral infections; infections with bacteria (extracellular or intracellular), such as in tuberculosis, leprosy, chlamydia, listeria, legionella and cholera and infection by E. coli, P. aeruginosa, S. aureus, Streptococcus spp., N. meningitidis and S. pyogenes and several other infections; infections by parasites, e.g. in malaria and leishmaniosis.

The antibodies may also be used for treatments in which antibody proteins are known to be useful. Such treatments include cancer, but also other disease groups, such as autoimmune diseases (rheumatoid arthritis, inflammatory bowel disease, etc.).

Other non-naturally occurring therapeutic proteins include cytotoxic molecules, e.g. to treat cancer.

In a third alternative, the mRNA may be used for regenerative purposes, e.g. to induce the local production of proteins that will help remodeling the target tissue in a desired way. Thus, for example, mRNA that encode factors that will promote proper healing in a wound (e.g. growth factors), or factors that will induce the formation of new blood vessels in ischemic tissues such as in the heart after an infarction, may be used. Another example is the use of mRNA to generate a pulse production of a paracrine factor to direct e.g. progenitor cells to differentiate in a way useful for generating a beneficial response, e.g. the regeneration of heart muscle and vessels after a heart infarction (Zangi et al., 2013, *Nat. Biotechnol.*, 31 (10), 898-907). Similar principles may be used e.g. for repair of damage to neural tissues (e.g. due to physical damage, brain thrombosis or in Alzheimer's or Parkinson's disease), for regeneration of tissues in the eye and in many other types of tissue damage.

In a particularly preferred embodiment, the disease to be treated is cancer. In this case protein therapy may be achieved in a number of ways (immunotherapy may also or alternatively be used as described hereinafter). For example, mRNA can be used for the local or systemic expression of proteins that modulate anti-tumour immune responses, such as checkpoint inhibitors (e.g. monoclonal antibodies encoded by mRNAs), ligands that will activate co-stimulatory molecules on immune cells (e.g. a CD40 ligand), or factors acting in a paracrine fashion to modulate the tumour microenvironment in a way that may enhance anti-tumour immune responses, e.g. by acting on tumour-infiltrating macrophages.

In immunotherapy methods the expressed polypeptide is used to generate a therapeutic immune response. This may include prophylactic or therapeutic vaccination methods. Such methods may be used to treat infectious diseases. For example, prophylactic vaccination may be used in which a relevant antigen is used prior to exposure to the infectious agent to generate adaptive immunity to subsequent exposure. Preferred target infectious diseases are typically diseases in which T-cell responses are important. Examples include: viral diseases such as influenza, hepatitis (e.g. B and C), HIV, Herpes and many other viral infections; infections with bacteria (intracellular or extracellular), such as in tuberculosis, leprosy, *chlamydia*, *listeria*, *legionella* and cholera and infection by *E. coli, P. aeruginosa, S. aureus, Streptococcus* spp., *N. meningitidis* and *S. pyogenes*, and several other infections; infections by parasites, e.g. in malaria and leishmaniosis. Appropriate antigens are selected to generate a prophylactic immune response and the encoding mRNA used in methods of the invention.

Therapeutic vaccination is also contemplated, i.e. treatment of infected subjects by generation of an immune response to antigen expressed after mRNA internalization. In this case, preferred target diseases are chronic infections by viruses, bacteria (usually intracellular but also extracellular) and parasites, such as those described above for prophylactic vaccination.

Of particular interest is the use of immunotherapy in treating cancer. This includes both prophylactic and therapeutic vaccination, as described hereinbefore.

Gene therapy methods may also be used. As referred to herein gene therapy methods are considered to be methods which introduce or modify one or more gene within a subject or modify the expression of one or more gene in a subject. Thus, by way of example, the mRNA may encode a polypeptide that would assist in altering the subject's genome. Thus, for example, mRNA which encodes enzymes useful in sequence-specific modification of the chromosomal DNA in the target cells may be used, e.g. to corrected a mutated gene or to insert a copy of a non-mutated version of a disease-causing mutated gene. Examples of such enzymes include Cas9 (CRISPR technology), zinc finger nucleases, transcription activator-like effector nuclease mRNA (TALEN mRNA) and site-specific recombinases. As necessary, in some cases the mRNA would be used together with a "donor DNA" e.g. to insert the "correct" DNA sequence to correct a mutation, in other cases the mRNA may be used alone, e.g. for inactivating a gene. In preferred aspects, the method may be used to treat Huntingdon's disease, cystic fibrosis and other inherited diseases.

As discussed above, in a particularly preferred aspect the method is used to generate an immune response, particularly to achieve vaccination. As referred to herein an immune response is any reaction of the host defence system in vivo. As referred to herein, "vaccination" is the use of an antigen (or a molecule containing an antigen) to elicit an immune response which is prophylactic or therapeutic against the development (or further development) of a disease, disorder or infection, wherein that disease, disorder or infection is associated with abnormal expression or presence of that antigen. Preferably the disease is cancer. In one embodiment the vaccination is therapeutic, for example in the treatment of cancers or chronic parasitic, bacterial or viral infections as described herein. In an alternative embodiment the vaccination is prophylactic, for example to prevent a cancer or to reduce further cancers developing following treatment of an earlier cancer with a therapeutic vaccination. In a further embodiment when an immune response to an infection is to be generated, e.g. an infection as discussed hereinbefore, e.g. a viral infection such as hepatitis or HIV infection, parasitic infections like malaria, or bacterial infections (e.g. tuberculosis), the vaccination is prophylactic in nature.

In methods of vaccination, the mRNA expresses a suitable antigenic molecule for vaccination purposes.

Many such antigens or antigenic vaccine components are known in the art and include all manner of bacterial or viral antigens or indeed antigens or antigenic components of any pathogenic species including protozoa or higher organisms. Whilst traditionally the antigenic components of vaccines have comprised whole organisms (whether live, dead or attenuated) i.e. whole cell vaccines, in addition sub-unit vaccines, i.e. vaccines based on particular antigenic components of organisms e.g. proteins or peptides, or even carbohydrates, have been widely investigated and reported in the literature. Any such "sub-unit"-based vaccine component may be used as the expressed polypeptide of the present invention.

However, the invention finds particular utility in the field of peptide vaccines, e.g. peptides of 5-500 e.g. 10 to 250 such as 15 to 75, or 8 to 25 amino acids.

A vast number of peptide vaccine candidates have been proposed in the literature, for example in the treatment of viral diseases and infections such as AIDS/HIV infection or influenza, canine parvovirus, bovine leukaemia virus, hepatitis, etc. (see e.g. Phanuphak et al., 1997, *Asian Pac. J. Allergy. Immunol.*, 15(1), 41-8; Naruse, 1994, *Hokkaido Igaku Zasshi*, 69(4), 811-20; Casal et al., 1995, *J. Virol.*, 69(11), 7274-7; Belyakov et al., 1998, *Proc. Natl. Acad. Sci. USA*, 95(4), 1709-14; Naruse et al., 1994, *Proc. Natl. Sci. USA*, 91(20), 9588-92; Kabeya et al., 1996, *Vaccine*, 14(12), 1118-22; Itoh et al., 1986, *Proc. Natl. Acad. Sci. USA*, 83(23) 9174-8. Similarly bacterial peptides may be used, as indeed may peptide antigens derived from other organisms or species.

In addition to antigens derived from pathogenic organisms, peptides have also been proposed for use as vaccines against cancer or other diseases such as multiple sclerosis. For example, mutant oncogene peptides hold great promise as cancer vaccines acting as antigens in the stimulation of cytotoxic T-lymphocytes. (Schirrmacher, 1995, *Journal of Cancer Research and Clinical Oncology*, 121, 443-451; Curtis, 1997, *Cancer Chemotherapy and Biological Response Modifiers*, 17, 316-327). A synthetic peptide vaccine has also been evaluated for the treatment of metastatic melanoma (Rosenberg et al., 1998, *Nat. Med.*, 4(3), 321-7), and personalized mRNA-based vaccines based on peptide epitopes mutated in tumours of individual patients have shown great promise for cancer treatment (Sahin et al., 2017, *Nature*, 257, 222-226). A T-cell receptor peptide vaccine for the treatment of multiple sclerosis is described in Wilson et al., 1997, *J. Neuroimmunol.*, 76(1-2), 15-28. Any such peptide vaccine component may be used as the expressed polypeptide according to the invention, as indeed may any of the peptides described or proposed as peptide vaccines in the literature. The mRNA used for vaccination may code for a single peptide antigen, or it may encode several different peptide antigens translated into one polypeptide, e.g. as described in Sahin et al., 2017, supra.

For administration of agents or cells described herein in vivo, any mode of administration common or standard in the art may be used, e.g. oral, parenteral (e.g. intramuscular, transdermal, subcutaneous, percutaneous, intraperitoneal, intrathecal or intravenous), intestinal, buccal, rectal or topical, both to internal and external body surfaces etc. The invention can be used in relation to any tissue which contains cells to which the photosensitising agent or the mRNA molecule (or cells containing the same) may be localized, including body fluid locations, as well as solid tissues. All tissues can be treated as long as the photosensitiser is taken up by the target cells, and the light can be properly delivered. When cells are to be administered methods are not constrained by the ability to deliver light. Preferred modes of administration are intradermal, intratumoural, subcutaneous, intramuscular or topical administration or injection, particularly intradermal or intratumoural administration. Preferably administration is topical (also referred to herein as local administration).

Thus, the compositions of the invention may be formulated in any convenient manner according to techniques and procedures known in the pharmaceutical art, e.g. using one or more pharmaceutically acceptable carrier or excipients. "Pharmaceutically acceptable" as referred to herein refers to ingredients that are compatible with other ingredients of the compositions as well as physiologically acceptable to the recipient. The nature of the composition and carriers or excipient materials, dosages etc. may be selected in routine manner according to choice and the desired route of administration, purpose of treatment etc. Dosages may likewise be determined in routine manner and may depend upon the nature of the molecule, purpose of treatment, age of patient, mode of administration etc. In connection with the photosensitising agent the potency/ability to disrupt membranes on irradiation, should also be taken into account.

To achieve the desired outcome, i.e. treatment or prevention of disease, disorder or infection, the methods or parts thereof may be repeated. Thus, the method in its entirety may be performed multiple times (e.g. 2, 3 or more times) after an appropriate interval or parts of the method may be repeated, e.g. further administration of the mRNA and/or photosensitising agent as defined herein or additional irradiation steps. For example, the method or part of the method may be performed again a matter of days, e.g. between 5 and 60 days (for example 7, 14, 15, 21, 22, 42 or 51 days), e.g. 7 to 20 days, preferably 14 days, or weeks, e.g. between 1 and 5 weeks (for example, 1, 2, 3 or 4 weeks) after it was first performed. All or part of the method may be repeated multiple times at appropriate intervals of time, e.g. every two weeks or 14 days. In a preferred embodiment the method is repeated at least once. In another embodiment the method is repeated twice.

The invention will now be described in more detail in the following non-limiting Examples with reference to the following drawings in which:

FIG. 1 shows the effect of PCI on intradermal mRNA delivery. The results of bio-luminescence imaging in animal 6 of Example 1A are shown. The animal was injected with a mixture of 2 μg luciferase mRNA (TriLink L-6107, 5meC, ψ) and 0.003 μg TPCS$_{2a}$ in sites A and D (top left and bottom right circles) and 2 μg mRNA only in sites B and C (top right and bottom left circles). 1 h after injection all injection sites were illuminated for 6 min with the LumiSource illumination device. 4 hours after illumination the luciferase expression was analysed by bio-luminescence imaging using the IVIS instrument. a. Image of the mouse showing the injection sites and the regions-of-interest. b. Quantitation of the bio-luminescence in the different regions of interest; horizontal black lines denote mean values.

Figure 2:
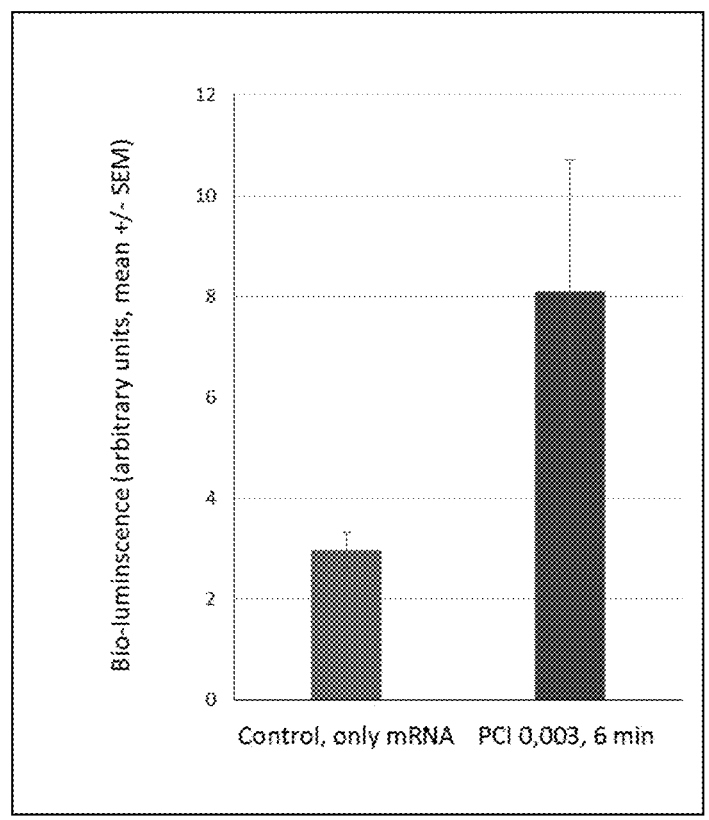

FIG. 2 shows a comparison of luciferase expression in all treated sites for Example 1A. The animals were injected with 2 μg luciferase mRNA (TriLink L-6107, 5meC, Y) alone or in combination with 0.003 μg TPCS$_{2a}$ according to Table 1. Animals were imaged for luciferase bio-luminescence in the IVIS instrument and bio-luminescence in the different ROIs was quantified as described under Methods. Mean values+/−standard error of the mean (n=12) are shown.

Figure 3:
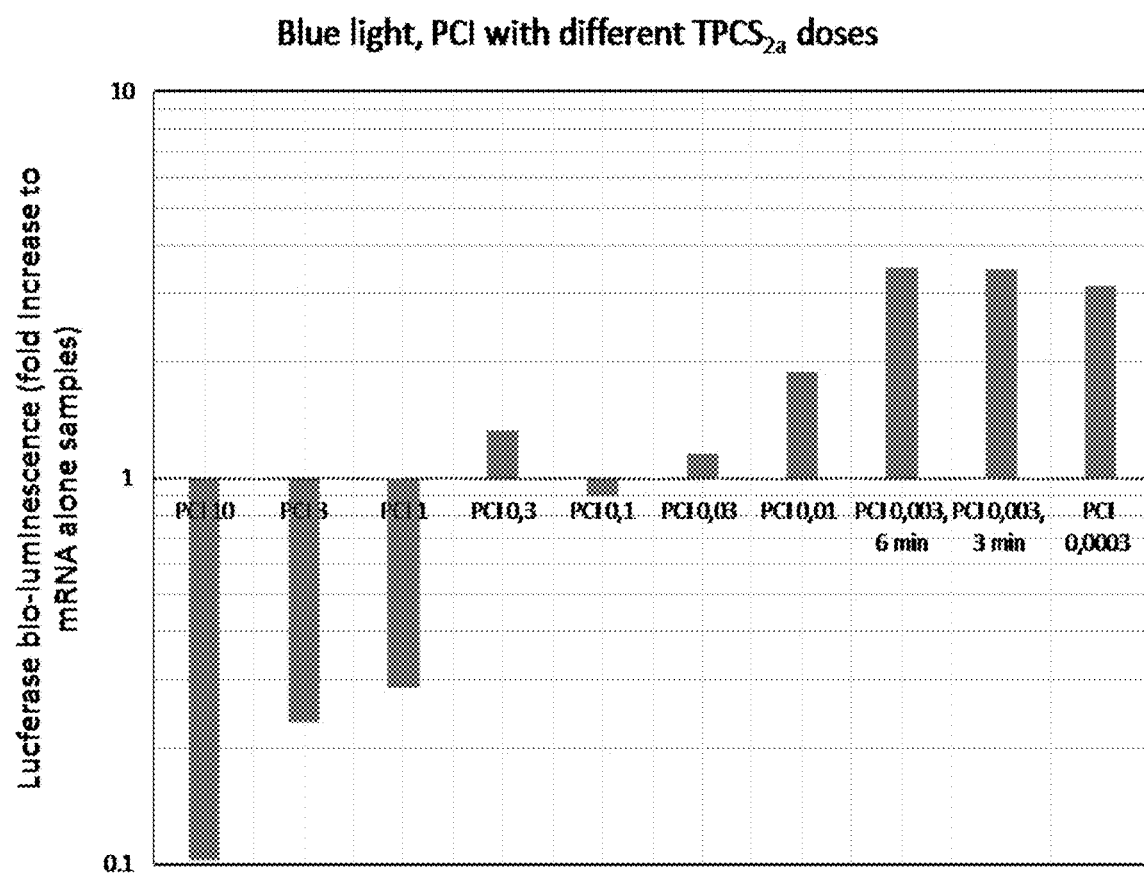

FIG. 3 shows the effects of different photosensitiser doses. 3 μg mRNA and different amounts of TPCS$_{2a}$ (indicated in the figure; PCI10 means PCI with a TPCS$_{2a}$ dose of 10 μg, etcetera) were mixed and injected into the skin of mice as described under Methods. 60 min after the injections the mice were illuminated for 6 (in general) or 3 min (indicated in the figure) with blue light. The animals were injected with luciferin and imaged in the IVIS instrument. For each animal the luminescence at the sites receiving mRNA+TPCS$_{2a}$ was compared to the luminescence at the sites receiving mRNA only, and the fold increase (FI) in luminescence at the TPCS$_{2a}$ injected sites in each animal was calculated.

Figure 4:
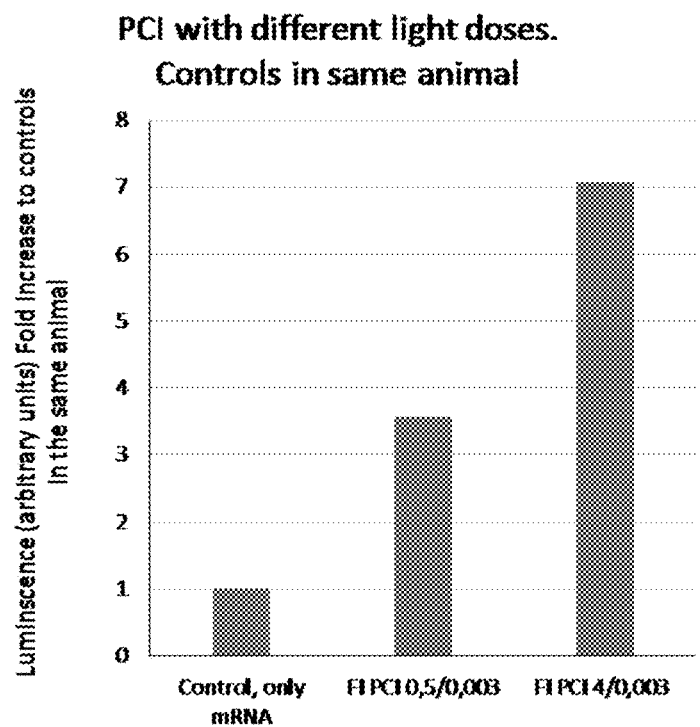

FIG. 4 shows the effects of different light doses. 2 μg mRNA and 0.003 μg TPCS$_{2a}$ mixed and injected into the skin of mice. 60 min after the injections the mice were illuminated for 0.5 or 4 min. The animals were injected with luciferin and imaged in the IVIS instrument. The luminescence in defined ROIs around the injection sites was quantified in the IVIS instrument. For each animal the luminescence at the sites receiving mRNA+TPCS$_{2a}$ was compared to the luminescence at the sites receiving mRNA only, and the fold increase (FI) in luminescence at the TPCS$_{2a}$ injected sites was calculated.

Figure 5:
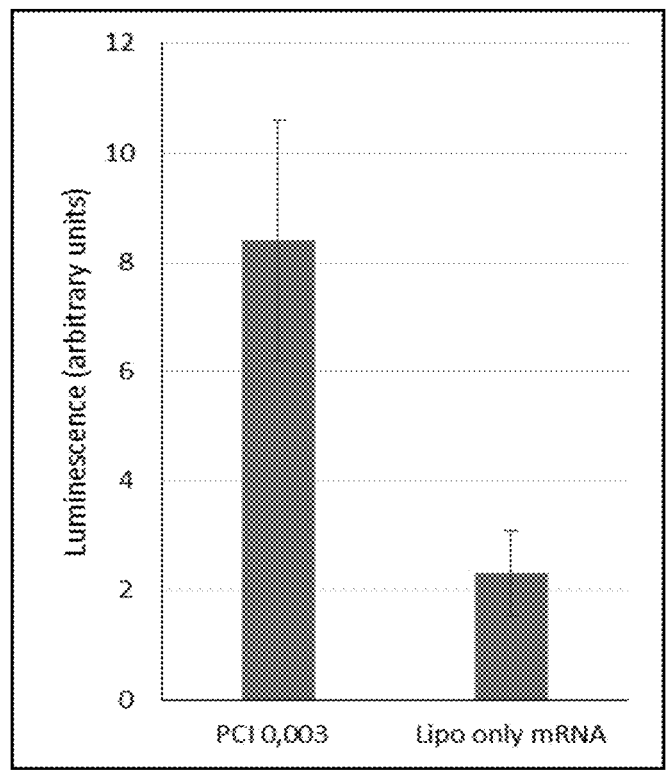

FIG. 5 shows the efficacy of the PCI method of intradermal mRNA delivery relative to the use of lipofectamine. The animals were treated according to Table 3. Animals were imaged for luciferase bio-luminescence in the IVIS instrument and bio-luminescence in the different ROIs was quantified as described. Mean values+/−standard error of the mean are shown. n=4 for "PCI 0.003" and 6 for "Lipo only mRNA".

Figure 6:
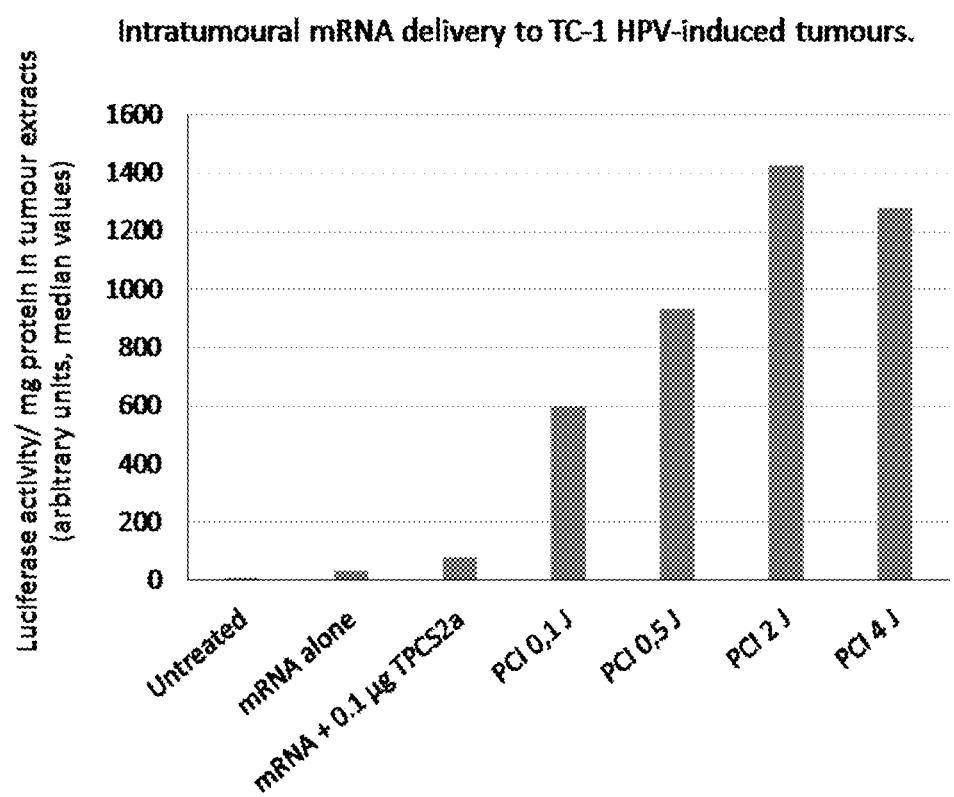

FIG. 6 shows the effect of PCI on mRNA delivery in tumours. Animals with TC-1 tumours were treated as described in Example 2 and Table 4. 20 hours after illumination the tumours were excised and homogenized, and the luciferase activity (RLU) and protein concentration were measured in the tumour homogenates. Results are shown as median RLU/mg protein for each group (n=3).

Figure 7:
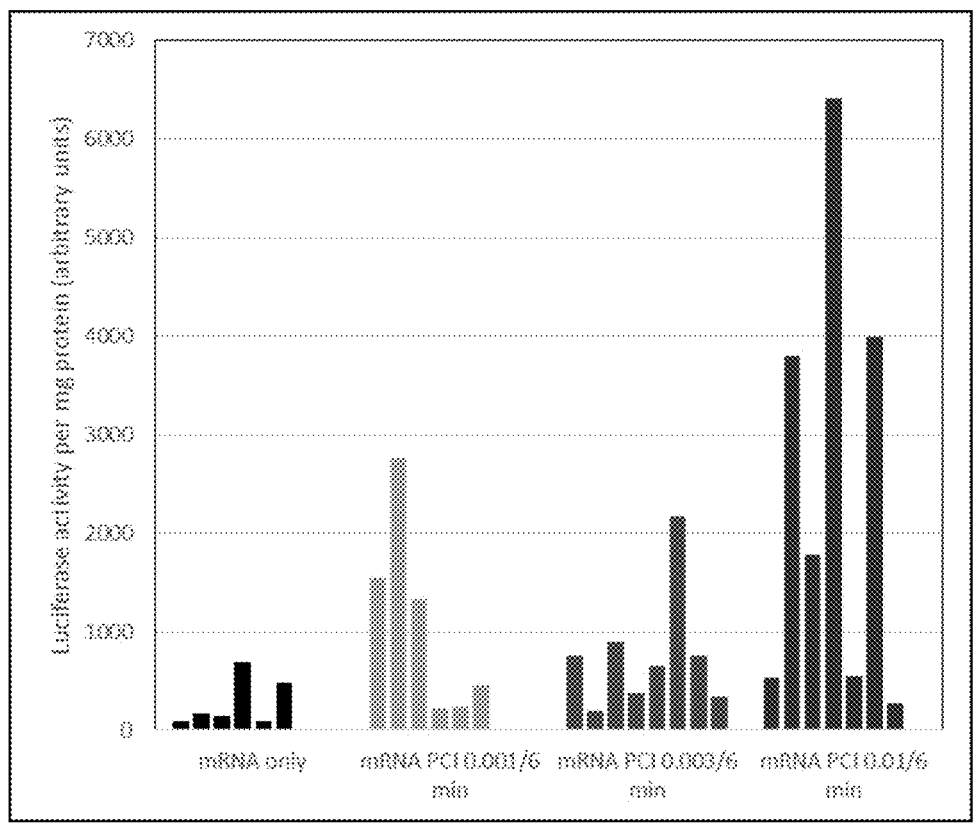
Figure 7:
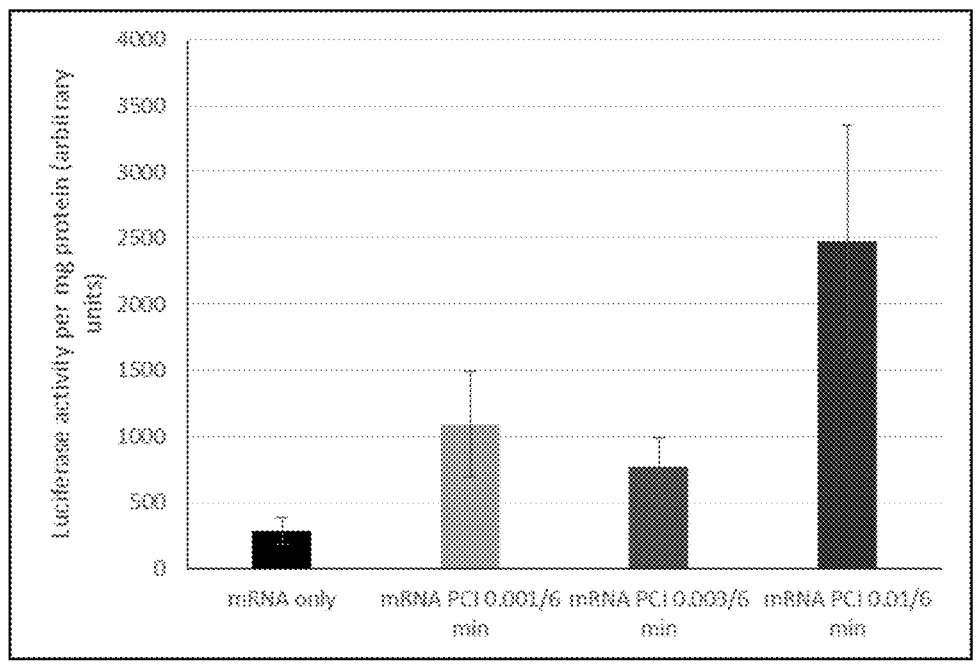

FIG. 7 shows the effect of PCI on mRNA delivery in tumours. Animals with MC-38 tumours were treated as described in Example 3 and Table 5. 20 hours after illumination the tumours were excised and homogenized, and the luciferase activity and protein concentration were measured in the tumour homogenates. A. Results of tumour delivery of luciferase mRNA in single tumours. B. Results of tumour delivery of luciferase mRNA as a mean±SEM for each experimental group.

Figure 8:
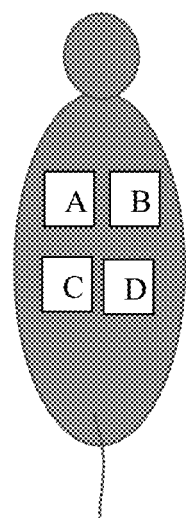

FIG. 8 shows the sites at which animals were injected by mRNA and $TPCS_{2a}$, as described under Methods and treated as described in Table 1.

EXAMPLES

Example 1: Intradermal mRNA Delivery In Vivo

Experiments were performed to study in vivo naked mRNA delivery to skin in mice.

Materials and Methods

Firefly luciferase mRNA (1921 nucleotides in length; L-6107—with modified bases 5-methylcytidine (5meC) and pseudo-uridine (ψ); L-6307—unmodified mRNA; L-7202—with modified base 5-methoxyuridine (5moU), and with the TriLink CleanCap™ modification as the capping structure, purchased from TriLink Biotechnologies, San Diego, USA) and $TPCS_{2a}$ (Amphinex®, PCI Biotech AS, Norway) were mixed in a volume of 20 μl PBS and the mixture was injected into the skin of mice at time 0. Different doses were used in different experiments, and in control samples no $TPCS_{2a}$ was used. Injections were performed in 4 sites (A-D) per mouse (see FIG. 1 and diagram and table below), and the injection sites were illuminated in general 60 min after mRNA/$TPCS_{2a}$ injection. With this set-up the two sites in each animal not receiving $TPCS_{2a}$ act as controls internal to each animal. This is useful for being able to correct for possible differences between animals e.g. in the injection and distribution of luciferin prior to the bio-luminescence imaging.

Injection sites were illuminated with blue light (wavelength between 400 and 540 nm with a peak at around 435 nm) from the LumiSource illumination device.

4-6 or 20-24 hours after illumination luciferase activity at the injection sites was analysed by bio-luminescence imaging in the IVIS instrument (IVIS Spectrum, model 124375R from PerkinElmer). Pictures were taken 20 min after luciferin injection, and bio-luminescence in a defined region-of-interest (ROI) around each injection site was quantified. The procedure for IVIS imaging was as follows:
i) The mice were given an intraperitoneal injection of 3 mg D-Luciferin (200 μl of 15 mg/ml stock).

ii) After approximately 10 min, the mice were anaesthetized by a subcutaneous injection of Zoletil (10-15 mg/kg xylasin, 5-10 mg/kg butorphanol and 15-20 mg/kg Zoletil (containing zolazepam and tiletamine)).

iii) 20 min after D-luciferin injection, mice were placed in the IVIS instrument and pictures were taken with automatic exposure of Luminescence (Andor camera IS0825R4582; iKon Living Image version: 4.5.2.18424. Binning factor: 8; Excitation filter: Block; Emission filter: Open; f Number: 1)

iv) The bio-luminescence in ROIs covering each injection site was measured to quantify luciferase expression. The detailed set-up of a typical experiment (Example 1) can be found in Table 1.

Example 1A: PCI Enhances Delivery of mRNA

Animals were injected by mRNA and $TPCS_{2a}$ as described under Methods and treated as described in Table 1 with the sites shown in FIG. 8.

TABLE 1

Set-up of the experiment in Example 1A. The different injection sites in each animal are shown in the diagram above.

| Animal no./site | Group name | mRNA (μg) | Amount of $TPCS_{2a}$ (μg) per injection. | Illumination (min blue light) |
|---|---|---|---|---|
| 1-A | Control, only mRNA | 2 | — | 6 |
| 1-B | PCI 0.003 B | 2 | 0.003 | 6 |
| 1-C | PCI 0.003 C | 2 | 0.003 | 6 |
| 1-D | Control, only mRNA | 2 | — | 6 |
| 2-A | PCI 0.003 A | 2 | 0.003 | 6 |
| 2-B | Control, only mRNA | 2 | — | 6 |
| 2-C | Control, only mRNA | 2 | — | 6 |
| 2-D | PCI 0.003 D | 2 | 0.003 | 6 |
| 3-A | Control, only mRNA | 2 | — | 6 |
| 3-B | PCI 0.003 B | 2 | 0.003 | 6 |
| 3-C | PCI 0.003 C | 2 | 0.003 | 6 |
| 3-D | Control, only mRNA | 2 | — | 6 |
| 4-A | PCI 0.003 A | 2 | 0.003 | 6 |
| 4-B | Control, only mRNA | 2 | — | 6 |
| 4-C | Control, only mRNA | 2 | — | 6 |
| 4-D | PCI 0.003 D | 2 | 0.003 | 6 |
| 5-A | Control, only mRNA | 2 | — | 6 |
| 5-B | PCI 0.003 B | 2 | 0.003 | 6 |
| 5-C | PCI 0.003 C | 2 | 0.003 | 6 |
| 5-D | Control, only mRNA | 2 | — | 6 |
| 6-A | PCI 0.003 A | 2 | 0.003 | 6 |
| 6-B | Control, only mRNA | 2 | — | 6 |
| 6-C | Control, only mRNA | 2 | — | 6 |
| 6-D | PCI 0.003 D | 2 | 0.003 | 6 |

Results

FIG. 1a shows bio-luminescence imaging for the four injection sites in a typical animal (animal 6 from Table 1). It can be seen that the sites subjected to PCI (sites A and D) exhibited significantly stronger luminescence than the control sites receiving mRNA only (B and C). This is also reflected in the quantitation of the luminescence in the ROIs (panel b) showing that in this animal the mean bio-luminescence for the PCI treated sites was more than 5 times higher than for the mRNA only sites.

FIG. 2 shows the mean values of the mRNA only and PCI-treated sites (12 sites of each) for all the animals in Example 1A. It can be seen that on the average the employment of PCI enhanced mRNA delivery about 3 times.

Example 1B: mRNA Delivery at Different Photosensitiser Doses

In Example 1B experiments were performed to further explore the $TPCS_{2a}$ dose response relationships for intradermal mRNA delivery in detail.

3 μg mRNA and different amounts of $TPCS_{2a}$ (ranging from 0.0003 μg to 10 μg) were mixed and injected into the skin of mice as described under Methods. 60 min after the injections the mice were illuminated for 6 (in general) or 3 min (in one case) with blue light from the LumiSource illumination device. The animals were injected with luciferin and imaged in the IVIS instrument as described under Methods. The luminescence in defined regions of interest round the injection sites was assessed in the IVIS instrument. For each animal the luminescence at the sites receiving mRNA+$TPCS_{2a}$ was compared to the luminescence at the sites receiving mRNA only, and the fold increase (FI) in luminescence at the $TPCS_{2a}$ injected sites in each animal was calculated by the formula FI=luminescence$_{mRNA+TPCS2a}$/luminescence$_{mRNA\ only}$.

Results

As can be seen from FIG. 3 with 6 min blue light illumination, PCI at $TPCS_{2a}$ doses above 0.3 µg had a strongly detrimental effect on mRNA delivery with a strong decrease in luciferase expression being observed (PCI10, PCI3 and PCI1). $TPCS_{2a}$ doses of 0.3 to 0.03 µg did not alter luciferase expression significantly as compared to what was obtained with mRNA alone, while at doses of 0.01 µg and below a significant enhancement of mRNA delivery was observed, also in accordance with what was found with the 0.003 µg dose in Example 1A. With the 0.003 µg dose also two different light doses were tested and it is apparent that a comparable enhancement of mRNA delivery was obtained with both 6 and 3 min illumination. Furthermore it can be seen that PCI also improved mRNA delivery at the even lower $TPCS_{2a}$ dose of 0.0003 µg.

Example 1C: mRNA Delivery at Different Light Doses

An experiment was performed to study the light dose relationship for mRNA delivery with PCI with 0.003 µg $TPCS_{2a}$. The Luciferase mRNA used was L-6307 FLuc unmodified mRNA from TriLink, 2 µg per injection. mRNA and $TPCS_{2a}$ were mixed and injected intradermally at time 0 at four sites per mouse (as described under Methods and in Table 2). The injection sites were illuminated 60 min after mRNA/$TPCS_{2a}$ injection, with blue light from the LumiSource illumination device. Illumination times of 0.5 of 4 min were used, and the efficacy of mRNA delivery was assessed by in vivo fluorescence imaging as described under Methods. The luminescence in defined ROIs around the injection sites was quantified in the IVIS instrument. For each animal the luminescence at the sites receiving mRNA+$TPCS_{2a}$ was compared to the luminescence at the sites receiving mRNA only, and the fold increase (FI) in luminescence at the $TPCS_{2a}$ injected sites was calculated by the formula FI=luminescence$_{mRNA+TPCS2a}$/luminescence$_{mRNA\ only}$.

TABLE 2

Set-up of the experiment in Example 1C.

| Animal no./site | Group name | mRNA (µg) | Amount of $TPCS_{2a}$ (µg) per injection. | Illumination (min blue light) |
|---|---|---|---|---|
| 1-A | Control, only mRNA | 2 | — | 0.5 |
| 1-B | PCI 0.5/0.003 B | 2 | 0.003 | 0.5 |
| 1-C | PCI 0.5/0.003 C | 2 | 0.003 | 0.5 |
| 1-D | Control, only mRNA | 2 | — | 0.5 |
| 2-A | PCI 0.5/0.003 A | 2 | 0.003 | 0.5 |
| 2-B | Control, only mRNA | 2 | — | 0.5 |
| 2-C | Control, only mRNA | 2 | — | 0.5 |
| 2-D | PCI 0.5/0.003 D | 2 | 0.003 | 0.5 |
| 3-A | Control, only mRNA | 2 | — | 4 |
| 3-B | PCI 4/0.003 B | 2 | 0.003 | 4 |
| 3-C | PCI 4/0.003 C | 2 | 0.003 | 4 |
| 3-D | Control, only mRNA | 2 | — | 4 |
| 4-A | PCI 4/0.003 A | 2 | 0.003 | 4 |
| 4-B | Control, only mRNA | 2 | — | 4 |
| 4-C | Control, only mRNA | 2 | — | 4 |
| 4-D | PCI 4/0.003 D | 2 | 0.003 | 4 |

Results

It can be seen from FIG. 4 that at a $TPCS_{2a}$ dose of 0.003 µg PCI enhanced mRNA delivery also with illumination times of 0.5 and 4 min. Taken together with the results with 6 min illumination (Examples 1A and 1B) this shows that with this photosensitiser dose PCI can induce mRNA delivery over a quite large light dose span, i.e. at least from 0.4 to 5 J/cm² blue light, as calculated from the known light output from LumiSource of about 13 mW/cm².

Example 1D: Comparison of PCI with mRNA Delivery with Lipofectamine

Lipofectamine is a very efficient transfection agent commonly used for delivery of mRNA and other nucleic acids; and it has also been used for mRNA delivery in vivo (Zangi et al., 2013, supra). However several type of toxic reactions have been observed with in vivo use of lipofectamine, limiting the possibilities for clinical use of this transfection agent. In this example the in vivo mRNA delivery with of PCI with naked mRNA was compared to what was achieved with lipofectamine. The experiment was performed as follows:

Modified Luciferase mRNA from TriLink (L-7202 CleanCap™ FLuc mRNA, 5moU modified) was used, 2 µg per injection.

mRNA was mixed with lipofectamine (Thermo Fisher Scientific, Waltham, MA, USA) or $TPCS_{2a}$ according to Table 3, and the mixtures were injected (20 µl injection volume) into the skin at time 0 in four sites per mouse. Some of the animals were illuminated for 6 min with blue light (LumiSource device) 60 min after lipofectamine/mRNA/$TPCS_{2a}$ injection (see Table 3).

mRNA translation was detected by IVIS imaging of luciferase bio-luminescence 4 hours after the illumination time point, and bioluminescence in the regions-of-interest was quantified (see Methods).

TABLE 3

Set-up of the experiment in Example 1D.

| Animal no./site | Group name | mRNA (µg) | Lipofectamine (µl) | Amount of $TPCS_{2a}$ (µg) per injection. | Illumination (min blue light) |
|---|---|---|---|---|---|
| 1-A | Control, only mRNA | 2 | — | — | 6 |
| 1-B | PCI 0.003 | 2 | — | 0.003 | 6 |
| 1-C | PCI 0.003 | 2 | — | 0.003 | 6 |
| 1-D | Control, only mRNA | 2 | — | — | 6 |
| 2-A | PCI 0.003 | 2 | — | 0.003 | 6 |
| 2-B | Control, only mRNA | 2 | — | — | 6 |
| 2-C | Control, only mRNA | 2 | — | — | 6 |
| 2-D | PCI 0.003 | 2 | — | 0.003 | 6 |
| 3-A | Control, only mRNA | 2 | — | — | — |
| 3-B | Lipo only mRNA | 2 | 6 | — | — |
| 3-C | Lipo only mRNA | 2 | 6 | — | — |
| 3-D | Control, only mRNA | 2 | — | — | — |
| 4-A | Lipo only mRNA | 2 | 6 | — | — |
| 4-B | Control, only mRNA | 2 | — | — | — |
| 4-C | Control, only mRNA | 2 | — | — | — |
| 4-D | Lipo only mRNA | 2 | 6 | — | — |
| 5-A | Control, only mRNA | 2 | — | — | — |

TABLE 3-continued

Set-up of the experiment in Example 1D.

| Animal no./site | Group name | mRNA (µg) | Lipofect-amine (µl) | Amount of TPCS$_{2a}$ (µg) per injection. | Illumination (min blue light) |
|---|---|---|---|---|---|
| 5-B | Lipo only mRNA | 2 | 6 | — | — |
| 5-C | Lipo only mRNA | 2 | 6 | — | — |
| 5-D | Control, only mRNA | 2 | — | — | — |

Results

It can be seen from FIG. 5 that for intradermal mRNA delivery PCI with 0.003 µg TPCS$_{2a}$ improved mRNA translation almost 4 times over what was achieved with lipofectamine.

Example 2: Intratumoural mRNA Delivery In Vivo with Red Light Illumination

An experiment was performed to study in vivo naked mRNA delivery to TC-1 tumours (model for HPV-induced tumours) in mice.

Materials and Methods

In these experiments the TC-1 tumour model for HPV-induced cancer was employed. mRNA delivery was assessed by performing a luciferase enzymatic assay on homogenates from tumours harvested the day after illumination. Red light laser light illumination with a wavelength of 652 nm was used. The experiment was performed as follows:

Luciferase mRNA (L-7202 CleanCap™ FLuc mRNA (5moU)) from TriLink, 3 µg per injection) was mixed with TPCS$_{2a}$ and injected into the tumours in an injection volume of 20 µl.

60 min after mRNA/TPCS$_{2a}$ injection the tumours were illuminated with different doses of red laser light (at 652 nm) for 12.5-500 seconds.

The day after illumination, all tumours were removed and frozen for later enzymatic assay for luciferase (Luciferase Assay System, Promega, Cat #E1500).

The protein content in the samples was measured with the RC DC Protein Assay kit (BioRad) assay, and the relative amounts of active luciferase in each sample was calculated as Relative Luminescence Units (RLU: Arbitrary units) per mg of protein.

The detailed set-up of the experiment is shown in Table 4.

TABLE 4

Set-up of the experiment in Example 2.

| Animal no. | Group name | TPCS$_{2a}$ (µg) | µg mRNA | Light dose (J/cm$^2$) |
|---|---|---|---|---|
| 1 | Untreated | — | — | No illum. |
| 2 | Untreated | — | — | No illum. |
| 3 | mRNA alone | — | 3 | No illum. |
| 4 | mRNA alone | — | 3 | No illum. |
| 5 | mRNA alone | — | 3 | No illum. |
| 6 | mRNA + 0.1 TPC | 0.1 | 3 | No illum. |
| 7 | mRNA + 0.1 TPC | 0.1 | 3 | No illum. |
| 8 | mRNA + 0.1 TPC | 0.1 | 3 | No illum. |
| 9 | PCI 0.1 J | 0.1 | 3 | 0.1 |
| 10 | PCI 0.1 J | 0.1 | 3 | 0.1 |
| 11 | PCI 0.1 J | 0.1 | 3 | 0.1 |
| 12 | PCI 0.5 J | 0.1 | 3 | 0.5 |
| 13 | PCI 0.5 J | 0.1 | 3 | 0.5 |
| 14 | PCI 0.5 | 0.1 | 3 | 0.5 |
| 15 | PCI 2 J | 0.1 | 3 | 2 |
| 16 | PCI 2 J | 0.1 | 3 | 2 |
| 17 | PCI 2 J | 0.1 | 3 | 2 |
| 18 | PCI 4 J | 0.1 | 3 | 4 |
| 19 | PCI 4 J | 0.1 | 3 | 4 |
| 20 | PCI 4 J | 0.1 | 3 | 4 |

Results

From FIG. 6 it can be seen from that with a TPCS$_{2a}$ dose of 0.1 µg, PCI induced a strong enhancement of mRNA delivery and translation. This effect was observed at all the illumination doses tested (from 0.1 to 4 J/cm$^2$), but seemingly with an optimum at around 2 J/cm$^2$. In comparison adding 0.1 µg TPCS$_{2a}$ without illuminating the tumours (the mRNA+0.1 µg TPCS$_{2a}$ group) did not seem to enhance mRNA delivery significantly over what was achieved with mRNA alone.

Example 3: Intratumoural mRNA Delivery In Vivo with Blue Light Illumination

An experiment was performed to study in vivo naked mRNA delivery to colon adenocarcinoma tumours (MC-38 tumours) in mice.

Materials and Methods

The experiment was performed with Luciferase-encoding modified mRNA, and the effect was analysed by an enzymatic luciferase assay on tumour extracts, with tumours harvested 20 hours after illumination. Each animal had two tumours (A and B) that were injected and analysed separately.

Materials

TPCS$_{2a}$ photosensitizer (PCI Biotech AS).
TriLink modified luciferase mRNA (T14-GU03A), 3 µg was used per injection.
Female mice of the strain C57BL/6 (Charles River) were be used. Animal identification and conditions of housing, acclimatisation, environment, diet and water was in accordance with the current Standard Operating Procedures at the animal facilities at Oslo University Hospital—The Radium Hospital.
Age and weight at start of dosing: 5-6 weeks, 18-20 g
MC-38 tumour cells (colon adenocarcinoma) were obtained from Kerafast (Boston, USA).

Experimental Procedure

The animals were inoculated with 500 000 MC-38 cells per tumour, 2 tumours per animal. The size of the tumours on mRNA injection was 60-150 mm$^3$. Animals were randomized by tumour volume, animals with tumour ulcers were excluded. mRNA was mixed with TPCS$_{2a}$ and the mixture (25 µl) was injected into the tumours at time 0. The pure (naked) mRNA was injected at the same time point.

The injections were performed with gas anesthesia (Sevoflurane). The aim of the injection was to deposit a solution in the centre of the outer third of the tumour, avoiding the central core of the tumour. Insulin syringes were used to deliver the 25 µl of treatment.

The tumours in the PCI groups were illuminated (blue light from LumiSource) 60 min after mRNA/TPCS$_{2a}$ injection according to Table 5. The day after mRNA administration (i.e. around 20 hours after illumination) animals were killed and all tumours were removed and frozen for later homogenization and enzymatic assay for luciferase (Luciferase Assay System, Promega, Cat #E1500). After homogenization the amount of protein in the tumour extract was determined using the RC-DC Protein Assay (Bio-Rad Hercules, California, USA) and the luciferase enzymatic activity per mg tumour was calculated.

The experimental groups were as set out in Table 5 below.

TABLE 5

Set-up of the experiment in Example 3.

| Animal no. (tumour (A or B)) | Group name | TPCS$_{2a}$ (µg) | naked mRNA (µg) | Illumination time (min) |
|---|---|---|---|---|
| 1A | mRNA only | — | 3 | — |
| 1B | mRNA only | — | 3 | — |
| 2A | mRNA only | — | 3 | — |
| 2B | mRNA only | — | 3 | — |
| 3A | mRNA only | — | 3 | — |
| 3B | mRNA only | — | 3 | — |
| 4A | mRNA PCI 0.003/6 min | 0.003 | 3 | 6 |
| 4B | mRNA PCI 0.003/6 min | 0.003 | 3 | 6 |
| 5A | mRNA PCI 0.003/6 min | 0.003 | 3 | 6 |
| 5B | mRNA PCI 0.003/6 min | 0.003 | 3 | 6 |
| 6A | mRNA PCI 0.003/6 min | 0.003 | 3 | 6 |
| 6B | mRNA PCI 0.003/6 min | 0.003 | 3 | 6 |
| 7A | mRNA PCI 0.003/6 min | 0.003 | 3 | 6 |
| 7B | mRNA PCI 0.003/6 min | 0.003 | 3 | 6 |
| 8A | mRNA PCI 0.001/6 min | 0.001 | 3 | 6 |
| 8B | mRNA PCI 0.001/6 min | 0.001 | 3 | 6 |
| 9A | mRNA PCI 0.001/6 min | 0.001 | 3 | 6 |
| 9B | mRNA PCI 0.001/6 min | 0.001 | 3 | 6 |
| 10A | mRNA PCI 0.001/6 min | 0.001 | 3 | 6 |
| 10B | mRNA PCI 0.001/6 min | 0.001 | 3 | 6 |
| 11A | mRNA PCI 0.01/6 min | 0.01 | 3 | 6 |
| 11B | mRNA PCI 0.01/6 min | 0.01 | 3 | 6 |
| 12A | mRNA PCI 0.01/6 min | 0.01 | 3 | 6 |
| 12B | mRNA PCI 0.01/6 min | 0.01 | 3 | 6 |
| 13A | mRNA PCI 0.01/6 min | 0.01 | 3 | 6 |
| 13B | mRNA PCI 0.01/6 min | 0.01 | 3 | 6 |
| 14A | mRNA PCI 0.01/6 min | 0.01 | 3 | 6 |
| 15A | mRNA PCI 0.01/6 min | 0.01 | 3 | 6 |

Results

As can be seen from FIG. 7A the employment of the PCI technology substantially enhanced luciferase mRNA delivery in MC38 tumours, manifested by a strongly increased luciferase enzymatic activity in the tumour homogenates. FIG. 7B shows the mean values for the different experimental groups, indicating PCI-induced improvements in mRNA delivery from about 3 (0.003/6 min group) to about 10 times (0.01/6 min group), as compared to the delivery of mRNA without using PCI.

The invention claimed is:

1. A pharmaceutical composition comprising an mRNA molecule and a photosensitising agent, wherein said mRNA molecule is naked and not bound or conjugated to or carried by any other component to aid its internalization and said photosensitising agent is a sulphonated meso-tetraphenyl chlorin, sulfonated tetraphenylporphine or a di- or tetrasulfonated aluminium phthalocyanine and is provided in the amount of 0.0001 to 0.1 µg and said mRNA is provided in an amount of 1 to 10 µg.

2. The pharmaceutical composition as claimed in claim 1, wherein said photosensitising agent is
 a) TPCS$_{2a}$ (tetraphenyl chlorin disulfonate) or a pharmaceutically acceptable salt thereof;
 b) in an amount of 0.001 to 0.1 µg; and/or
 c) at a concentration of 0.005 to 200 µg/ml.

3. The pharmaceutical composition as claimed in claim 2, wherein the photosensitising agent is at a concentration of 0.05 to 20 µg/ml.

4. The pharmaceutical composition as claimed in claim 1, wherein said mRNA molecule is at a concentration of 5 to 5000 µg/ml.

5. An in vivo method for introducing an mRNA molecule into the cytosol of a cell(s) in a subject, said method comprising
 i) contacting said cell(s) with an mRNA molecule and a photosensitising agent, wherein said mRNA is naked and not bound or conjugated to or carried by any other component to aid its internalization, and
 ii) irradiating the cell(s) with light of a wavelength effective to activate the photosensitising agent,
 wherein said photosensitising agent is a sulphonated meso-tetraphenyl chlorin, sulfonated tetraphenylporphine or a di- or tetrasulfonated aluminium phthalocyanine used in an amount of 0.0001 to 0.1 µg and said mRNA is used in an amount of 1 to 10 µg.

6. The method as claimed in claim 5 wherein said photosensitising agent is:
 (a) TPCS$_{2a}$ or a pharmaceutically acceptable salt thereof;
 (b) used in an amount of 0.001 to 0.1 µg; and/or
 (c) used at a concentration of 0.005 to 200 µg/ml.

7. The method as claimed in claim 5, wherein the mRNA molecule is from 50 to 10,000 nucleotides long.

8. The method as claimed in claim 5, wherein the mRNA is used at a concentration of 5 to 5000 µg/ml.

9. The method as claimed in claim 5, wherein said mRNA is expressed in said cell(s).

10. The method as claimed in claim 5, wherein said cell(s) is a mammalian cell(s) or a fish cell(s).

11. The method as claimed in claim 5, wherein the light has a wavelength of:
 a) 400-475 nm,
 b) 400-435 nm,
 c) 620-750 nm, or
 d) 640-660 nm.

12. The method as claimed in claim 5, wherein said contacting step is performed for:
 a) 30 minutes to 4 hours,
 b) 45 minutes to 90 minutes, or
 c) 60 minutes.

13. The method as claimed in claim 5, wherein the cell(s) is irradiated for:
 a) between 15 seconds and 60 minutes,
 b) for 0.5 to 12 minutes, or
 c) for 4 to 6 minutes.

14. The method as claimed in claim 5, wherein the cell(s) is irradiated with a light dose of from 0.01 to 50 J/cm$^2$.

15. The method as claimed in claim 5, wherein said cell(s) is contacted with said mRNA and photosensitising agent separately.

16. The method as claimed in claim 5, wherein said subject is a mammal or a fish.

17. The method as claimed in claim 5, wherein said mRNA and/or said photosensitising agent is administered locally, intradermally or intratumourally.

18. An in vivo method of expressing a polypeptide in a cell(s) in a subject, comprising introducing an mRNA molecule into a cell(s) of the subject by the method as defined in claim 5, wherein said mRNA molecule encodes said polypeptide.

19. A method of treating or preventing a disease, disorder or infection in a subject comprising introducing an mRNA molecule into one or more cells in vivo in said subject according to the method as defined in claim 5.

20. The method of treating or preventing a disease, disorder or infection as claimed in claim 19, wherein said disease, disorder or infection is one which would benefit from expression of one or more polypeptides.

21. The method of treating or preventing a disease, disorder or infection as claimed in claim 20 wherein an immune response is generated to said expressed polypeptide.

22. The method of treating or preventing a disease, disorder or infection as claimed in claim 20 wherein said disease is cancer or said infection is a viral or bacterial infection.

23. The method of treating or preventing a disease, disorder or infection as claimed in claim 20 wherein said mRNA and photosensitising agent is administered or is to be administered intradermally or intratumourally.

24. The method as claimed in claim 5 wherein said photosensitizing agent is used at a concentration of 0.05 to 20 µg/ml.

25. The method as claimed in claim 5, wherein said mRNA is expressed in said cell(s), wherein the polypeptide expressed by said mRNA is an antibody, a vaccine polypeptide or a cytotoxic molecule.

26. The method as claimed in claim 5, wherein said cell(s) is contacted with said mRNA and photosensitising agent simultaneously.

27. The method as claimed in claim 5, wherein said cell(s) is contacted with said mRNA and photosensitising agent sequentially.

28. The method as claimed in claim 5, wherein said subject is a human.

29. The method of treating or preventing a disease, disorder or infection as claimed in claim 20 wherein an immune response is generated to said expressed polypeptide, and said treatment or prevention occurs via prophylactic or therapeutic vaccination.

* * * * *